US009365885B2

(12) United States Patent
 Mak et al.

(10) Patent No.: US 9,365,885 B2
(45) Date of Patent: Jun. 14, 2016

(54) HIGH-THROUGHPUT COMPLEMENT-MEDIATED ANTIBODY-DEPENDENT AND OPSONIC BACTERICIDAL ASSAYS

(76) Inventors: Puiying Annie Mak, San Diego, CA (US); George Santos, Wayland, MA (US); Jeffrey Eugene Janes, San Diego, CA (US); John J. Donnelly, Moraga, CA (US)

( * ) Notice: Subject to any disclaimer, the term of this patent is extended or adjusted under 35 U.S.C. 154(b) by 95 days.

(21) Appl. No.: 12/816,534

(22) Filed: Jun. 16, 2010

(65) Prior Publication Data

US 2011/0312510 A1 Dec. 22, 2011

Related U.S. Application Data

(60) Provisional application No. 61/187,630, filed on Jun. 16, 2009.

(51) Int. Cl.
 *C12Q 1/00* (2006.01)
 *A01N 63/00* (2006.01)
 *C12Q 1/18* (2006.01)

(52) U.S. Cl.
 CPC ........................................ *C12Q 1/18* (2013.01)

(58) Field of Classification Search
 None
 See application file for complete search history.

(56) References Cited

U.S. PATENT DOCUMENTS 5,501,959 A    3/1996  Lancaster et al.
 6,812,172 B2 * 11/2004  Hayes et al. .................. 442/340

FOREIGN PATENT DOCUMENTS

WO    WO 2006/116325    * 11/2006    ............... C12N 1/21

OTHER PUBLICATIONS

Romero-Steiner et al., (Clin. And Diagn. Lab. Immuno. 2004. vol. 11(1):89-93).*
Mountzouros et al., (J. of Clin.Micrbio. 2000. vol. 38(8):2878-2884).*
Santos, G. et al. "Importance of complement source in measuring meningococcal bactericidal titers," Clinical and Diagnostic Laboratory Immunology, vol. 8, No. 3, 2001, pp. 616-623.
Mountzouros, K. et al. "Detection of complement-mediated antibody-dependent bactericidal activity in a fluorescence-based serum bactericidal assay for group B Neisseria meningitidis," Journal of Clinical Microbiology, vol. 38, No. 8, 2000, pp. 2878-2884.
Romero-Steiner, S. et al. "Measurement of serum bactericidal activity specific for Haemophilus influenzae type b by using a chromogenic and fluorescent metabolic indicator," Clinical and Diagnostic Laboratory Immunology, vol. 11, No. 1, 2004, pp. 89-93.
Bieging, K. et al. "Fluorescent multivalent opsonophagocytic assay for measurement of functional antibodies to *Streptococcus pneumoniae*," Clinical and Diagnostic Laboratory Immunology, vol. 12, No. 10, 2005, pp. 1238-1242.
Rodriguez, T. et al. "Standardization of Neisseria meningitidis serogroup B colorimetric serum bactericidal assay," Clinical and Diagnostic Laboratory Immunology, vol. 9, No. 1, 2002, pp. 109-114.

* cited by examiner

*Primary Examiner* — Rodney P Swartz
(74) *Attorney, Agent, or Firm* — Morrison & Foerster LLP

(57) ABSTRACT

The disclosure provides methods and kits for performing automated high-throughput assays to measure bactericidal activity in samples, such as plasma or sera from vaccinated subjects to evaluate the efficacy of vaccines against bacterial pathogens. The method combines obligatory linear-range data analysis, plate sealing and liquid volume handling for all assay steps to provide an automated, high-throughput measurement of bactericidal activity with favorable inter-assay and inter-operator variability.

38 Claims, 10 Drawing Sheets by sample, t=8

■ DU-02-01032
○ DU-02-01052
▼ DU-11-01006
◆ DU-11-01020
● DU-11-01052
□ DU-11-03010
   DU-12-03007
   DU-15-03010

5-99

| Time | 90% AFU |
|---|---|
| Slope | 0.7634 ± 0.02642 |
| Y-intercept when X=0.0 | 0.008342 ± 0.05067 |
| R squared | 0.9301 |

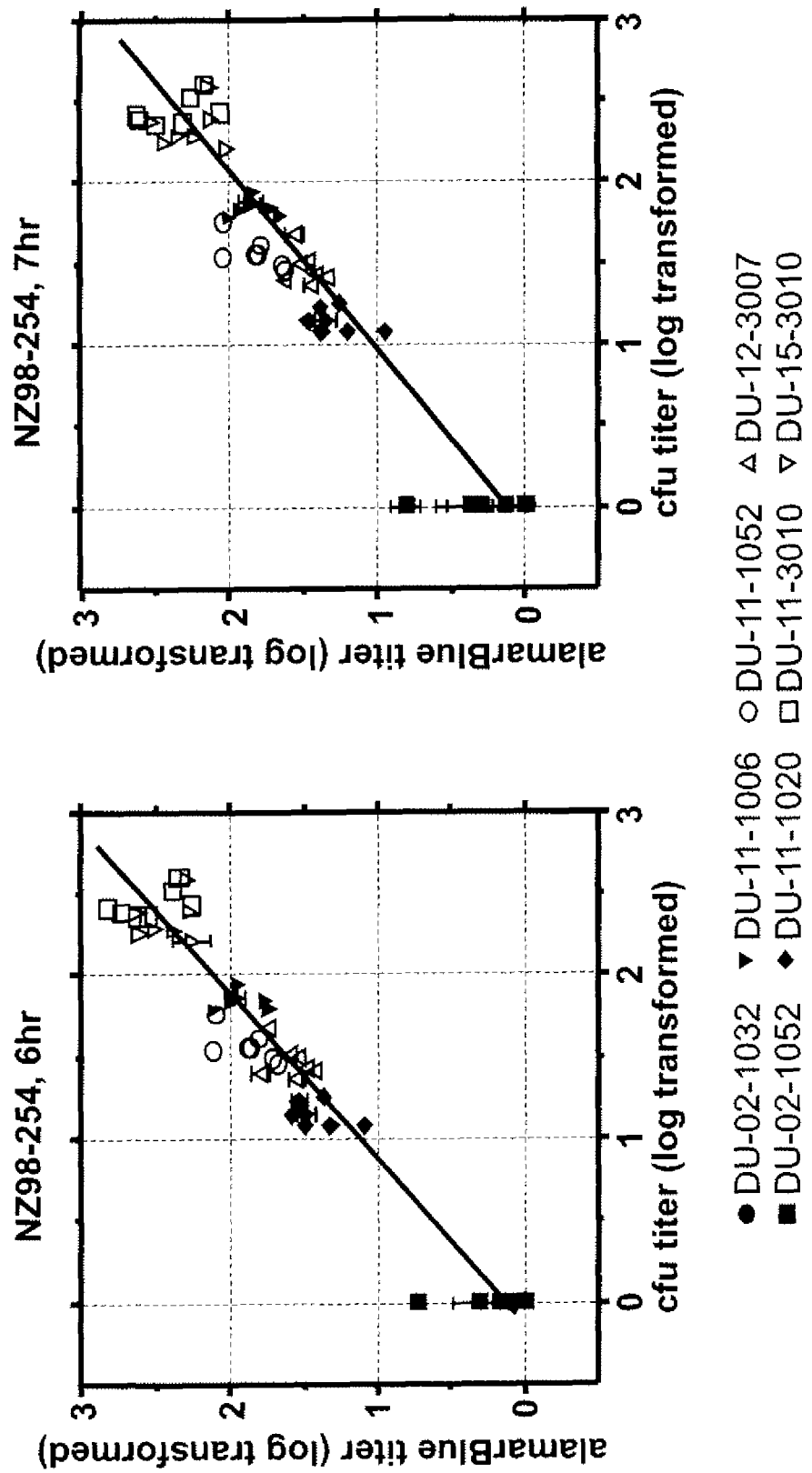

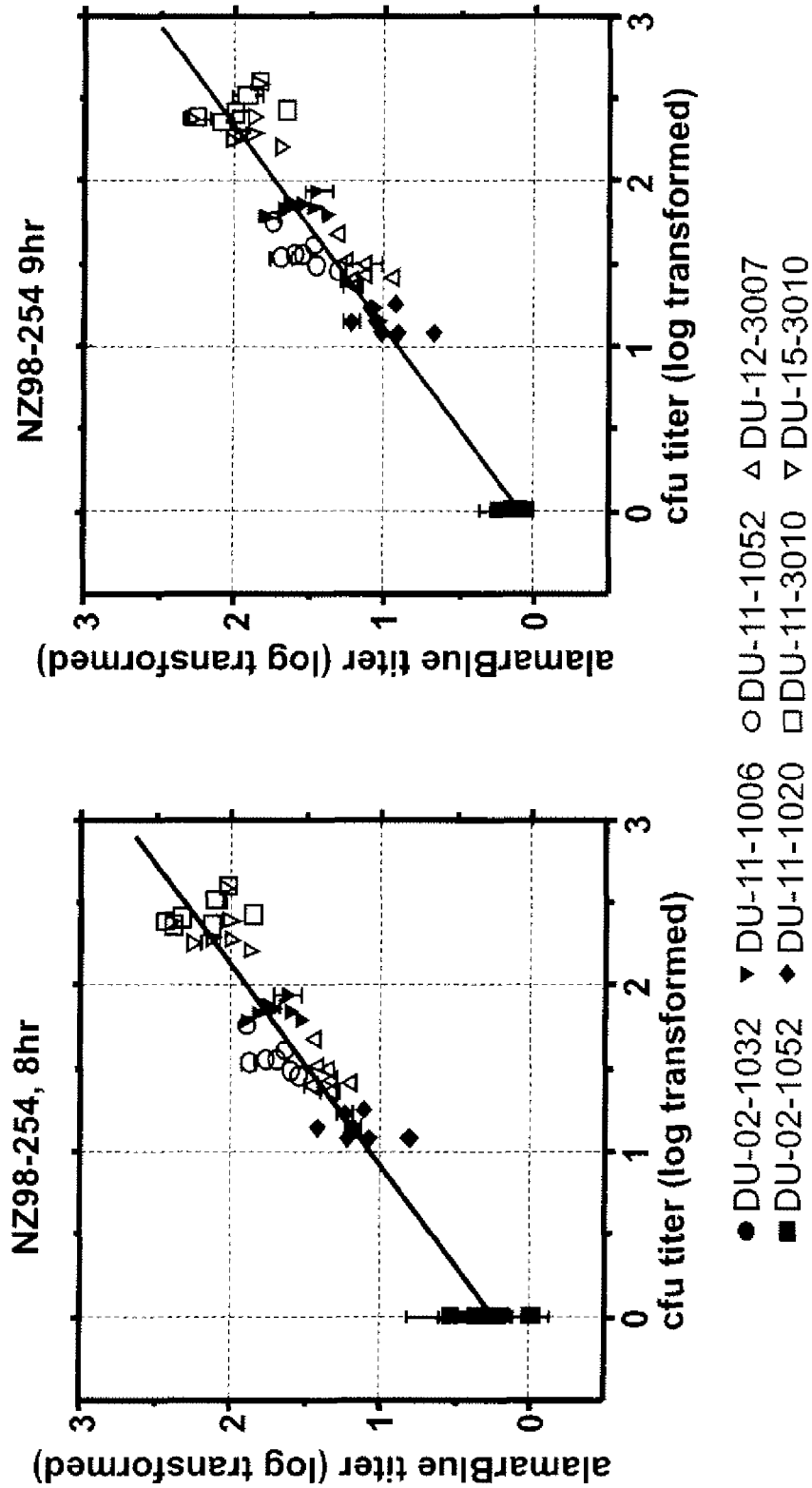
FIG. 6(iii)

HIGH-THROUGHPUT COMPLEMENT-MEDIATED ANTIBODY-DEPENDENT AND OPSONIC BACTERICIDAL ASSAYS

RELATED APPLICATION

This application claims the benefit under 35 U.S.C. §119(e) of U.S. Provisional Application No. 61/187,630, filed Jun. 16, 2009, which is incorporated herein in its entirety by reference.

GOVERNMENT SUPPORT

This invention was made in part with Government support under DTRA Grant No. HDTRA1-07-9-0001 awarded by the Department of Defense. The Government has certain rights in the invention.

FIELD OF THE INVENTION

The present invention relates to the field of measuring complement-associated and opsonic bactericidal activity and methods to assess the quality of the immune response. More specifically, the present invention relates to an automated high-throughput serum bactericidal assay to determine correlates of protection from functional anti-bacterial antibodies.

BACKGROUND

Bacterial infections and the resulting burden on society and health care management around the globe remains a tremendous challenge. Vaccines against important bacterial diseases such as MenACWY, MenB, group A Streptococcal (GAS) or Group B Streptococcal (GBS) disease, Streptococcus pneumoniae, Pseudomonas aeruginosa are currently in pre-clinical or clinical testing. The method currently employed by most laboratories for testing the efficacy of a vaccine involves testing clinical samples obtained from subjects inoculated with the vaccine for serum bactericidal activity (SBA) by counting surviving bacterial colony as a measure of the ability of a vaccine to induce a serum response in a vaccinated subject to effect killing of the bacterial pathogen tested. Functional assays such as a serum bactericidal assay are used as a proxy for efficacy based upon the assumption that if the subject has produced bactericidal antibodies against the pathogen above a specified level, then the subject is protected against infection by the organism and therefore that the vaccine may be used to protect others against the pathogen. These responses are measured in mice and humans and are a standard indicator of vaccine efficacy (e.g. see end-note 14 of reference (R5) below). Serum bactericidal activity measures bacterial killing mediated by complement, and can be assayed using human or animal complement, such as baby rabbit complement. WHO standards require a vaccine to induce at least a 4 fold rise in SBA in more than 90% of recipients when rabbit complement is used. Published studies (Goldschneider et al.) assigned an SBA titer of 1:4 using human complement as a correlate of protection against meningococcal disease. The functional assay and threshold as used today is typically an underestimate of a vaccine's efficacy, but such underestimate is deemed in the best interest of the public. Since the traditional SBA assay requires plating bacteria onto agar and counting surviving colony forming units (cfu) after an overnight incubation step, such assays are time consuming as the assays often take two or more days, are not simple to use and therefore problematic to standardize, and are labor-intensive resulting into low sample throughput. Thus the traditional SBA assays are not amenable to highly accurate and high-throughput rapid data analysis from clinical trials. In particular, due to the difficulty of assay standardization among labs, the generation of reliable data with large and multi-site clinical trials or from post-licensing surveillance can be problematic. Consequently there is an acute and long-felt need to develop a sensitive, high throughput bactericidal assay to enable a rapid and highly reproducible assessment of the efficacy of bacterial vaccine candidates.

The problems regarding the traditional SBA assay mentioned above have been recognized, but have not been solved. The usage of ALAMARBLUE™ (resazurin) has been initially described to measure the viability of cells exposed to poising agents (U.S. Pat. No. 5,501,959). Viable cells reduce ALAMARBLUE™ changing the color from blue to pink for colorimetric measurement and are emitting a fluorescence signal after excitation. For SBA assays the inclusion of ALAMARBLUE™ to measure fluorescence instead of counting surviving bacterial colonies was reported suggesting a good correlation between the traditional and the fluorescence based SBA assay (Mountzouros et al., 2000; Romero-Steiner et al., 2004).

However, until the present application the signal was either measured in plates using agar-containing medium (Mountzouros et al., 2000), which is unsuitable using automated liquid handlers, or only single end-point measurements were recorded (Romero-Steiner et al., 2004). Moreover, the reaction plates remained unsealed during the assay (Mountzouros et al., 2000; Romero-Steiner et al., 2004), increasing the risk of inconsistent results due to cross-contamination and evaporation. Thus, neither has to date been adapted into a commercially available high-throughput assay system to measure bactericidal activity, despite the long-felt and recognized need.

SUMMARY

To accurately measure the optimal fluorescence or colorimetric signal, recurrent plate reads are desirable so as to ensure that at least some of the measurements will be taken in the linear phase rather than the saturation phase of the fluorescent or colorimetric indicator. Particularly where the samples have an unknown bactericidal activity, such optimal readouts are desirable to be able to standardize the assay among different labs. Furthermore, in order to allow for automated handling of the assay, all assay compounds will preferably be liquid and not contain gelling agents, such as agar, which could interfere with the automation process. Lastly, since the plates are measured recurrent over a predetermined time period under potentially different environmental conditions, the sealing of plates, which may be done with optical lids to allow for fluorescence signal generation and reading without causing evaporation, is also a desirable component of the solution. The present disclosure addresses all these issues for the development of an automated fluorescent based high-throughput bactericidal assay.

One aspect includes a high-throughput method of assessing bactericidal activity of a sample which includes providing a sealed, non-gel fluid comprising an amount of a pathogen, a sample and a potentiator, wherein the fluid has been incubated for a time period sufficient for the sample to kill a portion of the pathogen if the sample comprises bactericidal or opsonic activity; measuring the metabolic indicator at three or more time points during a second incubation; and assessing the bactericidal activity using the measurements at the three or more time points. In certain embodiments, the metabolic indicator is a chromogenic compound or a fluorescent compound. In certain embodiments, the metabolic indicator is resazurin. In certain embodiments, the resazurin is ALAMARBLUE™. In certain embodiments which may be combined with any of the preceding embodiment, the pathogen is *N. meningitidis, N. gonorrhoeae, Streptococcus pyogenes, Streptococcus agalactiae, Streptococcus pneumoniae, H. influenzae, Staphylococcus aureus, Haemophilus influenza* B, *H. pylori*, meningitis/sepsis associated *E. coli*, Non-typeable *Haemophilus influenzae*, or uropathogenic *E. coli*. In certain embodiments which may be combined with any of the preceding embodiment, the potentiator is complement when assaying bactericidal activity or phagocytic cells and optionally complement when assaying opsonic activity. In certain embodiments, the phagocytic cells are neutrophils or macrophages. In certain embodiments which may be combined with any of the preceding embodiments that include phagocytic cells, the phagocytic cells are inactivated or removed from the fluid prior to the second incubation. In certain embodiments which may be combined with any of the preceding embodiments that include phagocytic cells, the metabolic indicator does not respond to the phagocytic cells' metabolic activity. In certain embodiments containing complement, complement is active complement or inactive complement. In certain embodiments, the active complement is derived from the group consisting of human, rabbit, baby-rabbit, other animal origin, or recombinant. In certain embodiments which may be combined with any of the preceding embodiment, the non-gel fluid contains no agarose or any other gelling agent used to form a solid growth surface for bacteria. In certain embodiments which may be combined with any of the preceding embodiment, the sealed, non-gel fluid is sealed prior to incubation of the pathogen and the sample and measurements to prevent evaporation of said fluid. In certain other embodiments which may be combined with any of the preceding embodiment, non-gel fluid is sealed after incubation of the pathogen and the sample and measurements to prevent evaporation of said fluid. In certain embodiments which may be combined with any of the preceding embodiment, the sealing comprises an optically clear seal to perform colorimetric and/or fluorimetric measurements without removal of said seal. In certain embodiments which may be combined with any of the preceding embodiment, the sample is an isolated antibody, serum or plasma of human or animal origin. In certain embodiments which may be combined with any of the preceding embodiment containing a serum or plasma sample, serum or plasma sample is obtained from a subject that was inoculated with a vaccine, a vaccine candidate or a vaccine component directed against the pathogen. In certain embodiments, the vaccine candidate or the vaccine component comprises one or more of a GNA1870 antigen, a GNA2132 antigen, and a NadA antigen. In certain embodiments which may be combined with any of the preceding embodiment, the sample is an isolated antibody, which may further be a recombinant antibody. In certain embodiments which may be combined with any of the preceding embodiment, the method includes at least two non-gel fluids, at least three, at least five, at least 10, wherein the second non-gel fluid (and each successive non-gel fluid) comprises a dilution of the sample in the first non-gel fluid (or preceding non-gel fluid). In certain embodiments, the dilution can be twofold, threefold, or fourfold or a repetitive dilution step of twofold dilution followed by twofold dilution, twofold dilution followed by threefold dilution, threefold dilution followed by threefold dilution, or fourfold dilution followed by fourfold dilution. In certain embodiments which may be combined with any of the preceding embodiment, the at least two (or more) non-gel fluids are incubated and measured in microtiter plates selected from the group consisting of 96, 384, and 1536 reaction wells per plate. In certain embodiments which may be combined with any of the preceding embodiment, the measuring step comprises repeated readings of said samples at predetermined time points for determination of a bactericidal antibody titer. In certain embodiments which may be combined with any of the preceding embodiment, the predetermined time points are selected from the group consisting of every minute, every hour and fractions thereof. In certain embodiments which may be combined with any of the preceding embodiment, at least three of said measured time points are in the linear measurement range of the metabolic indicator to measure the pathogen's growth. In certain embodiments which may be combined with any of the preceding embodiment, the measurements are fluorescence signals representing bacterial growth. In certain embodiments, the highest signal to noise ratio of between 1 to 99% or about 50% to about 80% of the fluorescence signal plateau is within linear measurement range of the metabolic indicator to measure the pathogen's growth. In certain embodiments which may be combined with any of the preceding embodiment, the assessing step can comprise assay optimization. In certain embodiments, the assay optimization comprises of a) signal development using a bacterial growth curve, b) time point determination for optimal signal to noise ratio, and, if applicable, c) correcting signal loss at high serum concentration by normalization with controls containing inactivated complement. In certain embodiments which may be combined with any of the preceding embodiment, the steps performed are fully automated. In certain embodiments, the interoperator variability of the fully automated assay is reduced compared to a traditional bactericidal assay. In certain embodiments which may be combined with any of the preceding embodiment, the number of processed samples by a single operator within a predetermined time period compared to the traditional bactericidal assay is increased at least threefold. In certain embodiments which may be combined with any of the preceding embodiments, the assessing step comprises correcting signal loss at high serum concentration by normalization with a control containing inactivated complement at a concentration approximately equal to the sample. In certain embodiments which may be combined with any of the preceding embodiments including more than one non-gel fluid, said assessing step comprises correcting signal loss at high serum concentration by normalization with at least two controls containing inactivated complement wherein the second control comprises a dilution of the first control that is equal to the dilution of the second non-gel fluid from the first non-gel fluid.

Another aspect includes a high-throughput method of assessing bactericidal activity of a sample including providing a sealed, agar-containing, fluid comprising an amount of a pathogen, a sample and a complement, wherein the fluid has been incubated for a time period sufficient for the sample to kill a portion of the pathogen if the sample comprises bactericidal activity; measuring the metabolic indicator at three or more time points during a second incubation; and assessing the bactericidal activity using the measurements at the three or more time points. In certain embodiments, the metabolic indicator is a chromogenic compound or a fluorescent compound. In certain embodiments, the metabolic indicator is resazurin. In certain embodiments, the resazurin is ALAMARBLUE™. In certain embodiments which may be combined with any of the preceding embodiment, the pathogen is *N. meningitidis, N. gonorrhoeae, Streptococcus pyo-* genes, *Streptococcus agalactiae, Streptococcus pneumoniae, H. influenzae, Staphylococcus aureus, Haemophilus influenzae* B, *H. pylori*, meningitis/sepsis associated *E. coli*, Nontypeable *Haemophilus influenzae* or uropathogenic *E. coli*. In certain embodiments which may be combined with any of the preceding embodiment, the potentiator is complement when assaying bactericidal activity or phagocytic cells and optionally complement when assaying opsonic activity. In certain embodiments, the phagocytic cells are neutrophils or macrophages. In certain embodiments which may be combined with any of the preceding embodiments that include phagocytic cells, the phagocytic cells are inactivated or removed from the fluid prior to the second incubation. In certain embodiments which may be combined with any of the preceding embodiments that include phagocytic cells, the metabolic indicator does not respond to the phagocytic cells' metabolic activity. In certain embodiments containing complement, the complement is active complement or inactive complement. In certain embodiments, the active complement is derived from the group consisting of human, rabbit, baby-rabbit, other animal origin, or recombinant. In certain embodiments which may be combined with any of the preceding embodiment, the sealed, fluid is sealed prior to incubation of the pathogen and the sample and measurements to prevent evaporation of said fluid. In certain other embodiments which may be combined with any of the preceding embodiment, fluid is sealed after incubation of the pathogen and the sample and measurements to prevent evaporation of said fluid. In certain embodiments which may be combined with any of the preceding embodiment, the sealing comprises an optically clear seal to perform colorimetric and/or fluorimetric measurements without removal of said seal. In certain embodiments which may be combined with any of the preceding embodiment, the sample is an isolated antibody, serum or plasma of human or animal origin. In certain embodiments which may be combined with any of the preceding embodiment containing a serum or plasma sample, serum or plasma sample is obtained from a subject that was inoculated with a vaccine, a vaccine candidate or a vaccine component directed against the pathogen. In certain embodiments, the vaccine candidate or the vaccine component comprises one or more of a GNA1870 antigen, a GNA2132 antigen, and a NadA antigen. In certain embodiments which may be combined with any of the preceding embodiment, the sample is an isolated antibody, which may further be a recombinant antibody. In certain embodiments which may be combined with any of the preceding embodiment, the method includes at least two fluids, at least three, at least five, at least 10, wherein the second fluid (and each successive fluid) comprises a dilution of the sample in the first fluid (or preceding fluid). In certain embodiments, the dilution can be twofold, threefold, or fourfold or a repetitive dilution step of twofold dilution followed by twofold dilution, twofold dilution followed by threefold dilution, threefold dilution followed by threefold dilution, or fourfold dilution followed by fourfold dilution. In certain embodiments which may be combined with any of the preceding embodiment, the at least two (or more) fluids are incubated and measured in microtiter plates selected from the group consisting of 96, 384, and 1536 reaction wells per plate. In certain embodiments which may be combined with any of the preceding embodiment, the measuring step comprises repeated readings of said samples at predetermined time points for determination of a bactericidal antibody titer. In certain embodiments which may be combined with any of the preceding embodiment, the predetermined time points are selected from the group consisting of every minute, every hour and fractions thereof. In certain embodiments which may be combined with any of the preceding embodiment, at least three of said measured time points are in the linear measurement range of the metabolic indicator to measure the pathogen's growth. In certain embodiments which may be combined with any of the preceding embodiment, the measurements are fluorescence signals representing bacterial growth. In certain embodiments, the highest signal to noise ratio of between 1 to 99% or about 50% to about 80% of the fluorescence signal plateau is within linear measurement range of the metabolic indicator to measure the pathogen's growth. In certain embodiments which may be combined with any of the preceding embodiment, the assessing step can comprise assay optimization. In certain embodiments, the assay optimization comprises of a) signal development using a bacterial growth curve, b) time point determination for optimal signal to noise ratio, and, if applicable, c) correcting signal loss at high serum concentration by normalization with controls containing inactivated complement. In certain embodiments which may be combined with any of the preceding embodiment, the steps performed are fully automated. In certain embodiments, the interoperator variability of the fully automated assay is reduced compared to a traditional bactericidal assay. In certain embodiments which may be combined with any of the preceding embodiment, the number of processed samples by a single operator within a predetermined time period compared to the traditional bactericidal assay is increased at least threefold. In certain embodiments which may be combined with any of the preceding embodiments, the assessing step comprises correcting signal loss at high serum concentration by normalization with a control containing inactivated complement at a concentration approximately equal to the sample. In certain embodiments which may be combined with any of the preceding embodiments including more than one fluid, said assessing step comprises correcting signal loss at high serum concentration by normalization with at least two controls containing inactivated complement wherein the second control comprises a dilution of the first control that is equal to the dilution of the second fluid from the first fluid.

Another aspect includes an assay for high-throughput assessing of bactericidal activity of a sample comprising a kit for practicing either of the preceding aspects in any and all of their various embodiments.

Another aspect includes computer-implemented methods of determining a bactericidal activity of a sample toward a pathogen, comprising obtaining, using a processor, a set of metabolic indicator measurements taken at a set incubation time point from a dilution series of incubation cultures, wherein the incubation cultures comprise an amount of the pathogen, complement, and a metabolic indicator and where each of the incubation cultures further comprise a different amount of the sample based upon a predetermined dilution series, wherein the set incubation time point corresponds to a time when the pathogen is rapidly growing in an incubation culture without bactericidal activity; obtaining, using the processor, a set of metabolic indicator measurements taken at the set incubation time point from a dilution series of normalization incubation cultures, wherein the dilution series of normalization incubation cultures corresponds to the dilution series of incubation cultures except that the dilution series of normalization incubation comprise no bactericidal activity; normalizing, using the processor, the set of metabolic indicator measurements using the set of normalizing measurements to produce a set of normalized metabolic indicator measurements; and determining, using the processor, the bactericidal activity of the sample by fitting a sigmoidal curve to the set of normalized metabolic indicator measurements to determine the dilution at which half-maximal growth inhibition occurs. In certain embodiments, the set incubation time point is determined, using the processor, by identifying in a growth curve of an incubation culture without bactericidal activity the two time points in the growth curve between which the metabolic indicator measurement increase is the greatest and setting the set incubation time point to be the later of the two time points. In other embodiments, the set incubation time point is determined, using the processor, by identifying in a growth curve of an incubation culture without bactericidal activity the saturation plateau of the metabolic indicator measurements and setting the set incubation time point to be the time in the growth curve when the metabolic indicator measurement is between 30% and 90% of the saturation plateau.

DETAILED DESCRIPTION OF THE PREFERRED EMBODIMENTS

Figure 1:
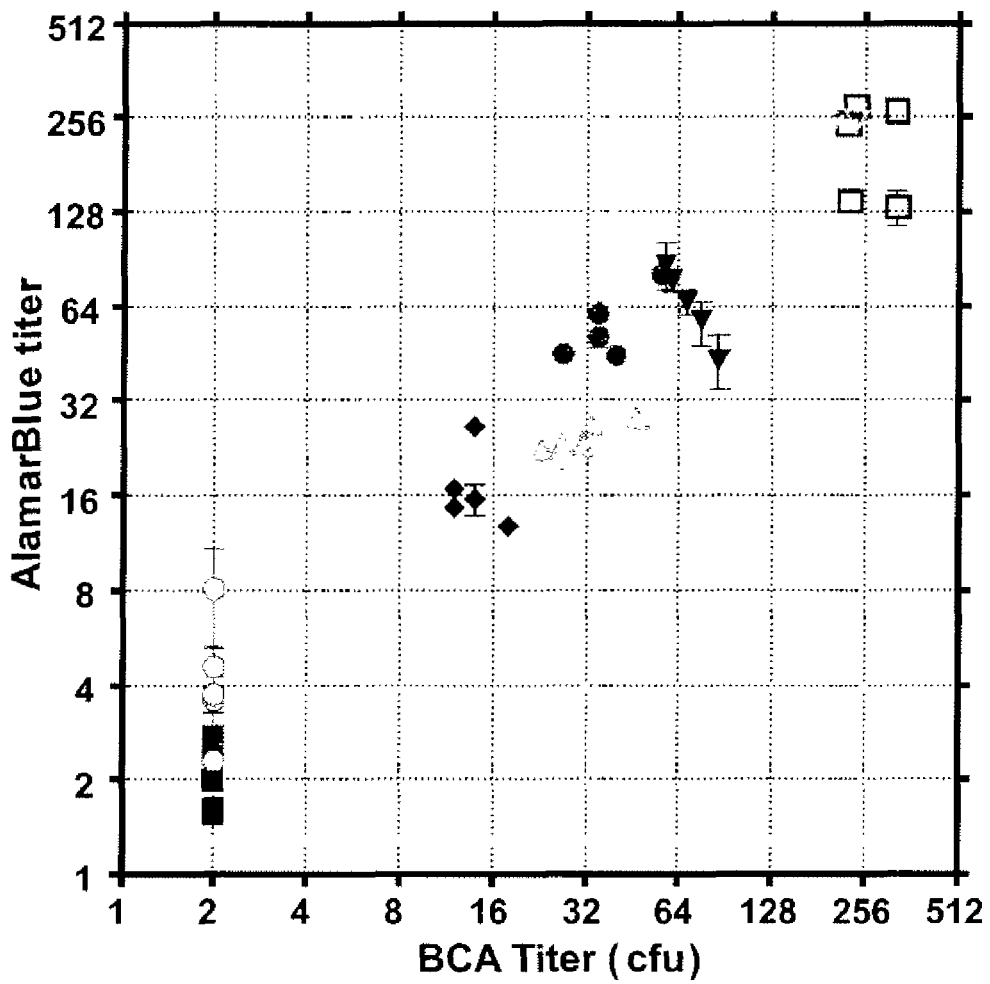
FIG. 1 shows a comparison of titers using standard and fluorescence readouts for the bactericidal assay. Human serum samples (legend) collected from clinical trial were tested in parallel with bactericidal assays which use cfu (x-axis) and ALAMARBLUE™ (y-axis) as readout. Each data point represents resulted from a concurrent test, and the samples were assayed on multiple dates. Each sample is assayed with no replicate in the traditional bactericidal assay (BCA) during the bactericidal reaction but the reaction mixture was plated twice for colony counting. The average of cfu values were used to calculate the interpolated titer. Any titer of <2 is plotted as 1.0 in the above graph. For the high-throughput (HT)-BCA, each serum sample was assayed in triplicate during the bactericidal reaction. The titer was calculated as described in text. The average of triplicate and standard deviation was plotted in the above graph.
Figure 2:
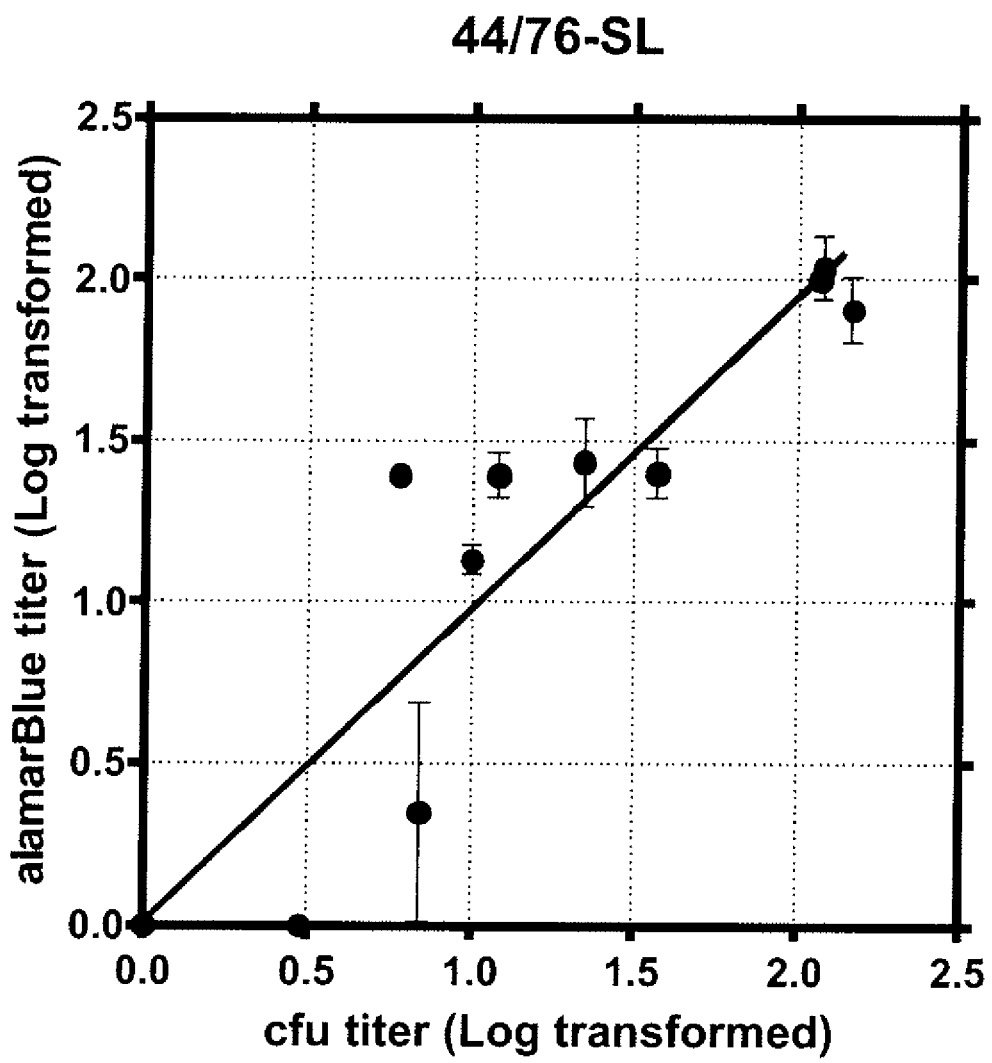
FIG. 2 demonstrates the comparison of titers resulting in a good correlation between standard and fluorescence readouts for the bactericidal assay using the MenB strain 44/76-SL. The data were collected from two paired assays, when each pair of standard and fluorescent BCA was run on the same day. Assays using human serum and plasma complement were combined for the analysis.
Figure 3:
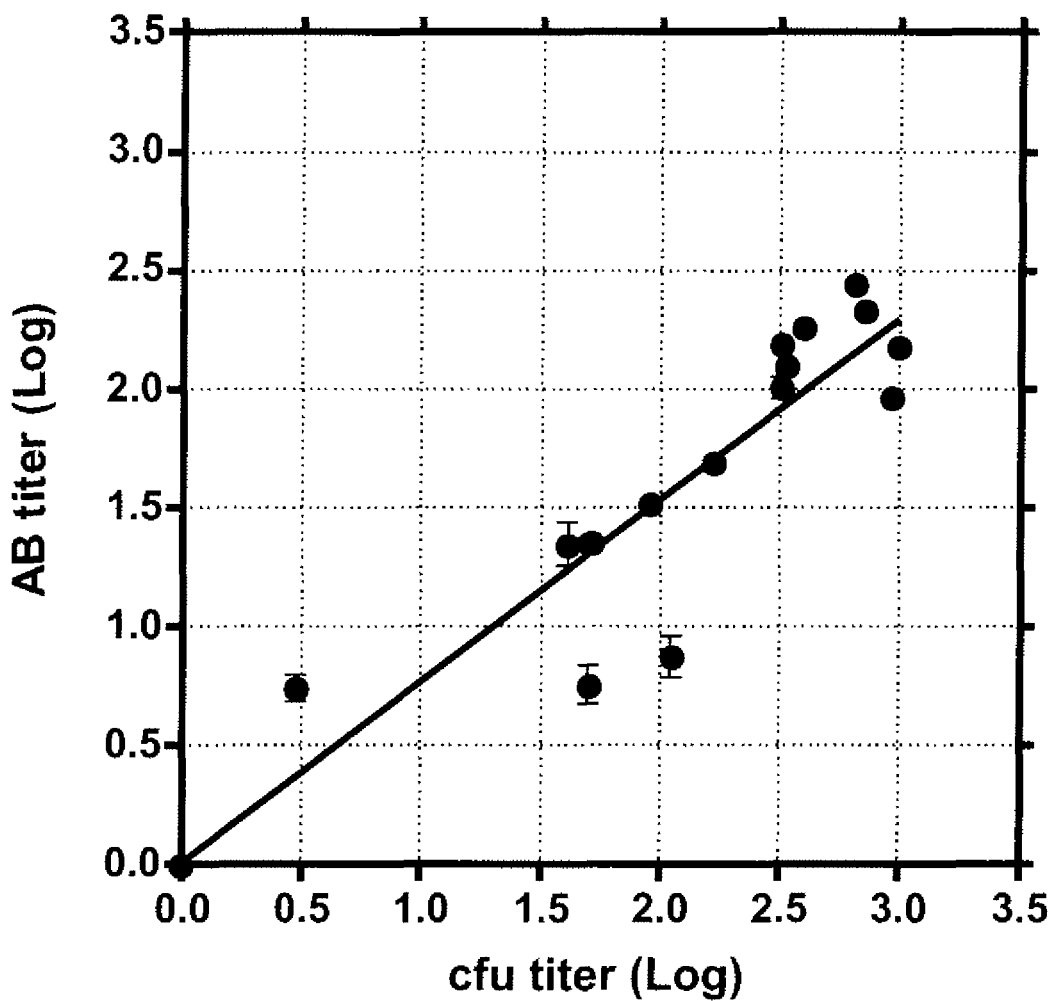
FIG. 3 shows the comparison of titers resulting in a good correlation between standard and fluorescence readouts for the bactericidal assay using the MenB strain 5/99. The data were collected from two paired assays, when each pair of standard and fluorescent BCA was run on the same day. Assays using human serum and plasma complement were combined for the analysis.

The disclosure provides methods, compositions, and kits for performing automated and/or high-throughput assays to measure bactericidal activity in samples, such as plasma or sera from vaccinated subjects or antibody preparations, to evaluate the efficacy of vaccines or passive immune therapies against bacterial pathogens. The automated and/or high-throughput assays disclosed herein meet a long-felt and yet previously unsolved need to allow for the automated and/or high-throughput handling of such assays which may additionally reduce inter-assay and inter-operator variability when evaluating bactericidal activity. In particular, the automated and/or high-through put assays may include recurrent sample reaction reads that preferably ensure that at least some measurements are taken in the linear range of the metabolic indicator while pathogen is in the log-phase of its growth (i.e., the metabolic indicator is not in its saturation phase and the pathogen is not in its lag phase or stationary phase). Such recurrent reads can be particularly advantageous for samples with an unknown bactericidal activity where an optimal readout is desirable so that the assays may be standardized among different labs or operators to improve accuracy and reproducibility of the data. Furthermore, implementing liquid compounds not containing gelling agents, such as agar, that could interfere with the automation process is another desirable aspect that may be combined with the other improvements disclosed herein. And since the sample reactions are measured recurrent over a predetermined time period under potentially different environmental conditions, the closure of plates with optical lids to allow for signal generation and reading without causing evaporation or cross-contamination between reaction wells is another desirable aspect that may be combined with the other aspects disclosed herein. Moreover, the potential of using plates that allow for an increased number of samples per plate than 96 well plates, such as 384 well plates, would not only increase the speed and efficiency by increased sample handling and inclusion of additional controls per plate, but would also reduce the reagent and sample volume, in order to reduce costs and to measure limited samples, such as collections from infants, and to allow for repeated measurements of the same sample. Thus, the present disclosure provides a method for an automated, high-throughput measurement of bactericidal activity which preferably includes improved inter-assay and inter-operator variability.

Vaccines and Passive Immune Therapeutics

The methods, compositions, and kits disclosed herein may be applied to any vaccines or passive immune therapeutics against bacterial pathogens as long as the bacterial pathogen is amenable to complement-mediated antibody-dependent bactericidal assays in general. The following embodiments are exemplary of the vaccines that may be assayed using the disclose methods, compositions and kits. Where particular components of a vaccine are mentioned such as capsular polysaccharides or protein antigens, one of skill in the art will understand that the assays disclosed herein may be used to assess efficacy of individual components by vaccination of a subject with the component as well as assess efficacy of the entire vaccine. The following list is both illustrative of the types of vaccines that may be assayed as well as the types of bacterial pathogens that may be included assayed.

In certain embodiments, the vaccines assayed include capsular saccharides from at least two of serogroups A, C, W135 and Y of *Neisseria meningitidis*. In other embodiments, such vaccines further comprise an antigen from one or more of the following: (a) *N. meningitidis*; (b) *Haemophilus influenzae* type B; *Staphylococcus aureus*, groups A and B *streptococcus*, pathogenic *E. coli*, and/or (c) *Streptococcus pneumoniae*.

In certain embodiments the vaccines assayed include serogroups C, W135 & Y of *N. meningitidis*. In certain embodiments the vaccines assayed include serogroups A, C, W135 & Y of *N. meningitidis*. In certain embodiments the vaccines assayed serogroups B, C, W135 & Y of *N. meningitidis*. In certain embodiments the vaccines assayed include serogroups A, B, C, W135 & Y of *N. meningitidis*. In certain embodiments the vaccines assayed include *H. influenzae* type B and serogroups C, W135 & Y of *N. meningitidis*. In certain embodiments the vaccines assayed include *H. influenzae* type B and serogroups A, C, W135 & Y of *N. meningitidis*. In certain embodiments the vaccines assayed include *H. influenzae* type B and serogroups B, C, W135 & Y of *N. meningitidis*. In certain embodiments the vaccines assayed include *H. influenzae* type B and serogroups A, B, C, W135 & Y of *N. meningitidis*. In certain embodiments the vaccines assayed *S. pneumoniae* and serogroups C, W135 & Y of *N. meningitidis*. In certain embodiments the vaccines assayed include *S. pneumoniae* and serogroups A, C, W135 & Y of *N. meningitidis*. In certain embodiments the vaccines assayed include *S. pneumoniae* and serogroups B, C, W135 & Y of *N. meningitidis*. In certain embodiments the vaccines assayed include *S. pneumoniae* and serogroups A, B, C, W135 & Y of *N. meningitidis*. In certain embodiments the vaccines assayed include *H. influenzae* type B, *S. pneumoniae* and serogroups C, W135 & Y of *N. meningitidis*. In certain embodiments the vaccines assayed include *H. influenzae* type B, *S. pneumoniae* and serogroups A, C, W135 & Y of *N. meningitidis*. In certain embodiments the vaccines formulations containing at least one compound of Formula (I) include *H. influenzae* type B, *S. pneumoniae* and serogroups B, C, W135 & Y of *N. meningitidis*. In certain embodiments the vaccines assayed include *H. influenzae* type B, *S. pneumoniae* and serogroups A, B, C, W135 & Y of *N. meningitidis*.

The methods and compositions disclosed herein can be used to determine efficacy of vaccines for various animals subjects including mammals such as human and non-human subjects, including, for example, pocket pets, fowl, and the like according to conventional methods well-known to those skilled in the art. Preferred vaccines will be vaccines with protein components which may be either recombinantly expressed or obtained from the pathogenic organism.

The methods and compositions disclosed herein can be used to assess manufacture of a vaccine to verify that each batch manufactured demonstrates requisite efficacy.

Suitable vaccines and/or pathogens that may be assayed using the methods and compositions disclosed herein include, but are not limited to, any material that raises a humoral immune response. Suitable vaccines assayed can include live bacterial antigens and inactivated bacterial antigens, toxoids, toxins, proteins, glycoproteins, peptides, and the like, numerous examples of which are described below. The vaccines may additionally include one or more adjuvants or other immunostimulatory compositions.

A. General Bacterial Pathogens and Vaccines Therefor

Bacterial pathogens and corresponding vaccines suitable for inducing bactericidal antibodies measured by assaying with the disclosed methods, compositions and kits include: vaccines based upon proteins, lipoproteins, proteoglycans, polysaccharides, lipopolysaccharides, and outer membrane vesicles which may be isolated, purified or derived from bacteria. In addition, vaccines may include bacterial lysates and inactivated bacteria formulations. Vaccines may include bacterial antigens produced by recombinant expression. Such bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitidis*: Meningitidis vaccines may include proteins (such as those identified in References 1-7, listed under [0092]), saccharides (including a polysaccharide, oligosaccharide or lipopolysaccharide), or outer-membrane vesicles (References 8, 9, 10, 11, listed under [0092]) purified or derived from *N. meningitidis* serogroup such as A, C, W135, Y, and/or B. *Meningitidis* protein antigens for use in vaccines may be selected from adhesions, autotransporters, toxins, Fe acquisition proteins, and membrane associated proteins (preferably integral outer membrane protein).

*Streptococcus pneumoniae*: *Streptococcus pneumoniae* vaccines may include a saccharide (including a polysaccharide or an oligosaccharide) and/or protein from *Streptococcus pneumoniae*. Saccharide antigens maybe selected from serotypes 1, 2, 3, 4, 5, 6B, 7F, 8, 9N, 9V, 1OA, HA, 12F, 14, 15B, 17F, 18C, 19A, 19F, 20, 22F, 23F, and 33F. Protein antigens may be selected from a protein identified in WO98/18931, WO98/18930, U.S. Pat. No. 6,699,703, U.S. Pat. No. 6,800,744, WO97/43303, and WO97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, SpIO1, Sp130, Sp125 or Sp133.

*Streptococcus pyogenes* (Group A *Streptococcus*): Group A *Streptococcus* vaccines may include a protein identified in WO02/34771 or WO05/032582 (including GAS 40), fusions of fragments of GAS M proteins (including those described in WO02/094851, and Dale, Vaccine (1999) 17:193-200, and Dale, Vaccine 14(10): 944-948), fibronectin binding protein (Sfbl), Streptococcal heme-associated protein (Shp), and Streptolysin S (SagA).

*Moraxella catarrhalis*: *Moraxella* vaccines include antigens identified in WO02/18595 and WO99/58562, outer membrane protein antigens (HMW-OMP), C-antigen, and/or LPS.

*Bordetella pertussis*: Pertussis vaccines include *pertussis* holotoxin (PT) and filamentous haemagglutinin (FHA) from *B. pertussis*, optionally also combination with pertactin and/or agglutinogens 2 and 3 antigen.

*Staphylococcus aureus*: *Staphylococcus aureus* vaccines include *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis: S. epidermidis* vaccines include slime-associated antigen (SAA).

*Clostridium tetani* (Tetanus): Tetanus vaccines include tetanus toxoid (TT), preferably used as a carrier protein in conjunction/conjugated with the compositions of the present invention.

*Corynebacterium diphtheriae* (Diphtheria): Diphtheria vaccines include diphtheria toxin, preferably detoxified, such as $CRM_{197}$. Additionally antigens capable of modulating, inhibiting or associated with ADP ribosylation are contemplated for combination/co-administration/conjugation with the compositions of the present invention. The diphtheria toxoids may be used as carrier proteins.

*Haemophilus influenzae* B (Hib): Hib vaccines include Hib protein antigens and Hib saccharide antigens.

*Pseudomonas aeruginosa: Pseudomonas* vaccines include endotoxin A, Wzz protein, *P. aeruginosa* LPS, more particularly LPS isolated from PAO1 (O5 serotype), and/or Outer Membrane Proteins, including Outer Membrane Proteins F (OprF)/

*Legionella pneumophila*: Bacterial vaccines may be derived from *Legionella pneumophila*.

*Streptococcus agalactiae* (Group B *Streptococcus*): Group B *Streptococcus* vaccines include a protein or saccharide antigen identified in WO02/34771, WO03/093306, WO04/041157, or WO05/002619 (including proteins GBS 80, GBS 104, GBS 276 and GBS 322, and including saccharide antigens derived from serotypes Ia, Ib, Ia/c, II, III, IV, V, VI, VII and VIII).

*Neisseria gonorrhoeae*: Gonorrhoeae vaccines include Por (or porin) protein, such as PorB (see Zhu et al, Vaccine (2004) 22:660-669), a transferring binding protein, such as TbpA and TbpB (See Price et al, Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see e.g. WO99/24578, WO99/36544, WO99/57280, WO02/079243).

*Chlamydia trachomatis*: *Chlamydia trachomatis* vaccines include antigens derived from serotypes A, B, Ba and C (agents of trachoma, a cause of blindness), serotypes L1, L2 & L3 (associated with *Lymphogranuloma venereum*), and serotypes, D-K. *Chlamydia trachomas* antigens may also include an antigen identified in WO00/37494, WO03/049762, WO03/068811, or WO05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis vaccines include TmpA antigen.

*Haemophilus ducreyi* (causing chancroid): *Ducreyi* vaccines include outer membrane protein (DsrA).

*Enterococcus faecalis* or *Enterococcus faecium*: Vaccines include a trisaccharide repeat or other *Enterococcus* derived antigens provided in U.S. Pat. No. 6,756,361.

*Helicobacter pylori*: *H. pylori* vaccines include Cag, Vac, Nap, HopX, HopY and/or urease antigen.

*Staphylococcus saprophyticus*: Vaccines include the 160 kDa haemagglutinin of *S. saprophyticus* antigen.

*Yersinia enterocolitica*: Vaccines include LPS (Infect Immun. 2002 August; 70(8): 4414).

*E. coli*: *E. coli* vaccines may be derived from meningitis/sepsis-associated *E. coli* (MNEC) (including antigens disclosed in WO06/089264), uropathogenic *E. coli* (UPEC) (including antigens disclosed in WO06/091517), enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC).

*Bacillus anthracis* (anthrax): *B. anthracis* vaccines are optionally detoxified and may be selected from A-components (lethal factor (LF) and edema factor (EF)), both of which can share a common B-component known as protective antigen (PA).

*Yersinia pestis* (plague): Plague vaccines include F1 capsular antigen, LPS, and *Yersinia pestis* V antigen).

*Mycobacterium tuberculosis*: Tuberculosis vaccines include lipoproteins, LPS, BCG antigens, a fusion protein of antigen 85B (Ag85B) and/or ESAT-6 optionally formulated in cationic lipid vesicles (Infect Immun. 2004 October; 72(10): 6148), *Mycobacterium tuberculosis* (Mtb) isocitrate dehydrogenase associated antigens, and/or MPT51 antigens (Infect Immun. 2004 July; 72(7): 3829).

*Rickettsia*: Vaccines include outer membrane proteins, including the outer membrane protein A and/or B (OmpB) (Biochim Biophys Acta. 2004 Nov. 1; 1702(2): 145), LPS, and surface protein antigen (SPA) (J Autoimmun. 1989 June; 2 Suppl:81).

*Listeria monocytogenes*: Bacterial vaccines may be derived from *Listeria monocytogenes*.

*Chlamydia pneumoniae*: Vaccines include those identified in WO02/02606.

*Vibrio cholerae*: Vaccines include proteinase antigens, LPS, particularly lipopolysaccharides of *Vibrio cholerae* II, O1 Inaba O-specific polysaccharides, *V. cholera* O139, antigens of IEM108 vaccine {Infect Immun. 2003 October; 71(10):5498-504), and/or Zonula occludens toxin (Zot).

*Salmonella typhi* (typhoid fever): Vaccines include protein antigens and capsular polysaccharides preferably conjugates (Vi, i.e., vax-TyVi).

*Borrelia burgdorferi* (Lyme disease): Vaccines include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein) VlsE Antigenic Variation Protein.

*Porphyromonas gingivalis*: Vaccines include *P. gingivalis* outer membrane protein (OMP).

*Klebsiella*: Vaccines include an OMP, including OMP A, or a polysaccharide optionally conjugated to tetanus toxoid.

Further bacterial vaccines of the disclosure may include capsular antigens, polysaccharide antigens or protein antigens of any of the above. Further bacterial vaccines may also include an outer membrane vesicle (OMV) preparation. When using an OMV, preferred bactericidal antibodies may be raised against a dominant epitope on the OMV such as PorA in the case of *N. meningitidis*. Additionally, vaccines include live, attenuated, and/or purified versions of any of the aforementioned bacteria. The vaccines may be derived from gram-negative or gram-positive bacteria. The vaccines may be derived from aerobic or anaerobic bacteria.

Additionally, any of the above bacterial-derived saccharides in a vaccine (polysaccharides, LPS, LOS or oligosaccharides) can be conjugated to another agent or antigen, such as a carrier protein (for example $CRM_{197}$). Such conjugation may be direct conjugation effected by reductive amination of carbonyl moieties on the saccharide to amino groups on the protein, as provided in U.S. Pat. No. 5,360,897 and Can J Biochem Cell Biol. 1984 May; 62(5):270-5. Alternatively, the saccharides can be conjugated through a linker, such as, with succinamide or other linkages provided in Bioconjugate Techniques, 1996 and CRC, Chemistry of Protein Conjugation and Cross-Linking, 1993.

B. STD Causing Bacteria and Vaccines Therefor

Additional pathogens and vaccines that may be assayed with the methods and compositions disclosed herein include pathogens that cause a sexually transmitted disease (STD). Such vaccines may provide for prophylaxis or therapy for STD's such as *chlamydia, gonorrhoeae,* syphilis and/or chancroid (See, WO00/15255). Vaccines may include antigens derived from one or more bacterial STD's. Pathogens causing STDs assayable hereunder include *Neisseria gonorrhoeae, Chlamydia trachomatis, Treponema pallidum, Haemophilus ducreyi, E. coli,* and *Streptococcus agalactiae.* Examples of specific vaccines against these pathogens and components of such vaccines are described above.

C. Respiratory Disease Causing Bacteria and Vaccines Therefor

Additional pathogens and vaccines that may be assayed with the methods, compositions and kits disclosed herein include pathogens which causes respiratory disease. For example, pathogens which cause respiratory disease include *Streptococcus pneumoniae, Pseudomonas aeruginosa, Bordetella pertussis, Mycobacterium tuberculosis, Mycoplasma pneumoniae, Chlamydia pneumoniae, Bacillus anthracis,* and *Moraxella catarrhalis.* Examples of specific vaccines against these pathogens and components of such vaccines are described above.

D. Pediatric Vaccine

Additional pathogens and vaccines that may be assayed with the methods, compositions and kits disclosed herein include pathogens against which pediatric subjects are vaccinated. Applying the methods and assays disclosed herein to pediatric vaccines, bactericidal antibodies assayed may have been obtained from similar pediatric subjects or a model organism for such pediatric subjects. Pediatric subjects are typically less than about 3 years old or less than about 2 years old or less than about 1 year old. Pediatric vaccines may include antigens derived from bacteria which may target pediatric populations and/or bacteria from which pediatric populations are susceptible to infection. Exemplary pathogens include *Streptococcus pneumoniae, Neisseria meningitidis, Streptococcus pyogenes* (Group A *Streptococcus*), *Moraxella catarrhalis, Bordetella pertussis, Staphylococcus aureus, Clostridium tetani* (Tetanus), *Corynebacterium diphtheriae* (Diphtheria), *Haemophilus influenzae* B (Hib), *Pseudomonas aeruginosa, Streptococcus agalactiae* (Group B *Streptococcus*), and *E. coli.* Examples of specific vaccines against these pathogens and components of such vaccines are described above.

E. Vaccines for Use in Elderly or Immunocompromised Individuals

Additional vaccines that may be assayed with the methods, compositions, and kits disclosed herein include one or more antigens suitable for use in elderly or immunocompromised individuals. Exemplary pathogens include *Neisseria meningitidis, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Corynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Chlamydia pneumoniae.* Examples of specific vaccines against these pathogens and components of such vaccines are described above.

G. *Neisseria Meningitidis* Serogroup B

A preferred pathogen is *N. meningitidis* serogroup B. Two examples of preferred vaccine for *N. meningitidis* serogroup B are (i) a five component vaccine comprising three primary components: NadA, GNA1870 and GNA2132; and two accessory components GNA1030 and GNA2091. In certain embodiments, the accessory components may be fused to the primary components, preferably GNA1030 is fused to the C-terminus of GNA2132 and GNA1870 is fused to the C-terminus of GNA2091. Additional disclosure regarding the five component vaccine may be found in WO04/032958. In certain embodiments, the five component vaccine may be combined with a membrane preparation derived from a *N. meningitidis* serogroup B strain, preferably an OMV membrane preparation.

NadA antigens. 'NadA' (Neiserrial adhesin A) from serogroup B of *N. meningitidis* is disclosed as protein '961' in reference (R3) (SEQ IDs 2943 & 2944) and as 'NMB1994' in reference (R2) (see also GenBank accession numbers: 11352904 & 7227256). A detailed description of the protein can be found in reference (R9). There is no corresponding protein in serogroup A ((R1), (R9)).

NadA may take various forms in vaccines. Preferred forms of NadA are truncation or deletion variants, such as those disclosed in references (R6), (R7), and (R8). In particular, NadA without its C terminal membrane anchor is preferred (e.g., deletion of residues 351 405 for strain 2996), which is sometimes distinguished herein by the use of a 'C' superscript, e.g., NadA$^{(C)}$. Expression of NadA without its membrane anchor domain in *E. coli* results in secretion of the protein into the culture supernatant with concomitant removal of its 23 mer leader peptide (e.g., to leave a 327 mer for strain 2996). Polypeptides without their leader peptides are sometimes distinguished herein by the use of a 'NL' superscript, e.g., NadA$^{(NL)}$ or NadA$^{(C)(NL)}$. NadA occurs in three main allelic variants as shown in FIG. 9 of reference (R10).

Vaccines may also comprise fragments which comprise an epitope from NadA in which case, detection of the epitope in a pathogen of interest may be performed using a monoclonal antibody to the epitope.

Secreted NadA can conveniently be prepared in highly pure form from culture supernatant by a process comprising the steps of: concentration and diafiltration against a buffer by ultrafiltration; anionic column chromatography; hydrophobic column chromatography; hydroxylapatite ceramic column chromatography; diafiltration against a buffer; and filter sterilisation. Further details of the process are given in the examples.

NadA is preferably used in an oligomeric form (e.g., in trimeric form).

GNA1870 Antigens. 'GNA1870' protein from serogroup B is disclosed as protein '741' in reference (R3) (SEQ IDs 2535 & 2536) and as 'NMB1870' in reference (R2) (see also GenBank accession number GI:7227128). The corresponding protein in serogroup A (R1) has GenBank accession number 7379322. GNA1870 is naturally a lipoprotein.

When as an antigen in a vaccine, GNA1870 protein may take various forms. Preferred forms of GNA1870 are truncation or deletion variants, such as those disclosed in references (R6), (R7), and (R8). In particular, the N terminus of GNA1870 may be deleted up to and including its poly-glycine sequence (i.e., deletion of residues 1 to 72 for strain MC58), which is sometimes distinguished herein by the use of a 'ΔG' prefix. This deletion can enhance expression. The deletion also removes GNA1870's lipidation site.

Allelic forms of GNA1870 may also be used as antigens and examples of alleles can be found in SEQ IDs 1 to 22 of reference (R8), and in SEQ IDs 1 to 23 of reference (R11). SEQ IDs 1-299 of reference (R12) give further GNA1870 sequences.

Vaccines may also comprise fragments which comprise an epitope from GNA1870 in which case, detection of the epitope in a pathogen of interest may be performed using a monoclonal antibody to the epitope.

Protein GNA1870 is an extremely effective antigen for eliciting anti meningococcal antibody responses, and it is expressed across all meningococcal serogroups. Phylogenetic analysis shows that the protein splits into two groups, and that one of these splits again to give three variants in total (R13), and while serum raised against a given variant is bactericidal within the same variant group, it is not active against strains which express one of the other two variants, i.e., there is intra-variant cross protection, but not inter variant cross protection. Through the use of monoclonal or polyclonal antibodies specific to one variant or another, one of skill in the art could differentiate between these groups. For maximum cross-strain efficacy, therefore, it is preferred that a vaccine should include more than one variant of protein GNA1870 and therefore the corresponding detection antibodies should take into account the nature of the vaccine. For example, a vaccine composition with one of each group will likely need at least a monoclonal antibody from each variant for detection.

GNA2091 Antigens. 'GNA2091' protein from serogroup B is disclosed as protein '936' in reference (R3) (SEQ IDs 2883 & 2884) and as 'NMB2091' in reference (R2) (see also GenBank accession number GI:7227353). The corresponding gene in serogroup A (R1) has GenBank accession number 7379093.

When used as an antigen in a vaccine, GNA2091 protein may take various forms. Preferred forms of GNA2091 are truncation or deletion variants, such as those disclosed in references (R6), (R7), and (R8). In particular, the N terminus leader peptide of GNA2091 may be deleted (i.e., deletion of residues 1 to 23 for strain MC58) to give GNA2091$^{(NL)}$.

GNA2091 antigens may also include variants (e.g., allelic variants, homologs, orthologs, paralogs, mutants etc).

Vaccines may also comprise fragments which comprise an epitope from GNA2091 in which case, detection of the epitope in a pathogen of interest may be performed using a monoclonal antibody to the epitope.

GNA1030 Antigens. 'GNA1030' protein from serogroup B is disclosed in as '953' in reference (R3) (SEQ IDs 2917 & 2918) and as 'NMB1030' in reference (R2) (see also GenBank accession number GI:7226269). The corresponding protein in serogroup A (R1) has GenBank accession number 7380108.

When used according to the present invention, GNA1030 protein may take various forms. Preferred forms of GNA1030 are truncation or deletion variants, such as those disclosed in references (R6), (R7), and (R8). In particular, the N terminus leader peptide of 953 may be deleted (i.e., deletion of residues 1 to 19 for strain MC58) to give 953$^{(NL)}$.

GNA1030 antigens may also include variants (e.g., allelic variants, homologs, orthologs, paralogs, mutants, etc.). Allelic forms of GNA1030 can be seen in FIG. 19 of reference (R4).

Vaccines may also comprise fragments which comprise an epitope from GNAT 1030 in which case, detection of the epitope in a pathogen of interest may be performed using a monoclonal antibody to the epitope.

GNA2132 Antigens. '287' protein from serogroup B is disclosed as '287' in reference (R3) (SEQ IDs 3103 & 3104), as 'NMB2132' in reference (R2), and in reference (R5) (see also GenBank accession number GI:7227388). The corresponding protein in serogroup A (R1) has GenBank accession number 7379057.

When used according to the present invention, GNA2132 protein may take various forms. Preferred forms of GNA2132 are truncation or deletion variants, such as those disclosed in references (R6), (R7), and (R8). In particular, the N terminus of GNA2132 may be deleted up to and including its poly glycine sequence (i.e., deletion of residues 1 to 24 for strain MC58), which is sometimes distinguished herein by the use of a 'ΔG' prefix. This deletion can enhance expression.

GNA2132 antigens may also include variants (e.g., allelic variants, homologs, orthologs, paralogs, mutants, etc.). Allelic forms of GNA2132 can be seen in FIGS. 5 and 15 of reference (R4), and in example 13 and FIG. 21 of reference (R3) (SEQ IDs 3179 to 3184).

Strains. Preferred antigens for *N. meningitidis* serogroup B vaccines are from strains 2996, MC58, 95N477, and 394/98. Strain 394/98 is sometimes referred to herein as 'NZ', as it is a New Zealand strain.

GNA2132 is preferably from strain 2996 or, more preferably, from strain 394/98.

GNA1870 is preferably from serogroup B strains MC58, 2996, 394/98, or 95N477, or from serogroup C strain 90/18311. Strain MC58 is more preferred.

Antigens GNA2091, GNA1030 and NadA are preferably from strain 2996.

Hypervirulent lineages and bactericidal antibody responses. In general, vaccines against *N. meningitidis* serogroup B will be able to induce serum bactericidal antibody responses after being administered to a subject who may be verified by testing in the bactericidal assay disclosed herein.

Rather than offering narrow protection, vaccines against *N. meningitidis* serogroup B induce bactericidal antibody responses against more than one hypervirulent lineage of serogroup B; however, even within a particular hypervirulent lineage, a vaccine may not be effective against all strains in the lineage. Therefore one of skill in the art would want an assay such as disclosed herein to determine if a vaccine is effective against particular strain of interest before using the vaccine.

References for the *N. meningitidis* serogroup B vaccines:

(R1) Parkhill et al. (2000) Nature 404:502-506.

(R2) Tettelin et al. (2000) Science 287:1809-1815.

(R3) WO99/57280.

(R4) WO00/66741.

(R5) Pizza et al. (2000) Science 287:1816-1820.

(R6) WO01/64920.

(R7) WO01/64922.

(R8) WO03/020756.

(R9) Comanducci et al. (2002) J. Exp. Med. 195:1445-1454.

(R10) WO03/010194.

(R11) UK patent application 0227346.4.

(R12) WO03/063766.

(R13) Masignani et al. (2003) J Exp Med 197:789-799.

Purified or Isolated Bactericidal Antibodies

The methods and compositions disclosed herein can be used to assess bactericidal activity of purified polyclonal antibodies or isolated monoclonal antibodies. These antibodies, if confirmed to provide effective bactericidal activity, may be used for passive immunization or as therapeutic vaccines against bacterial pathogens including any of the pathogens as described above, or as a calibration standard or positive control in bactericidal assays. Furthermore, to generate such polyclonal or monoclonal bactericidal antibodies any vaccines and components as described above may be used.

Opsonic Activity of Antibodies

The determination of antibacterial activity resulting in pathogen killing in subjects can also be determined by the opsonic activity of pathogen-specific antibodies resulting in the destruction by phagocytes. Bacterial pathogens as disclosed herein can be used to assess the opsonic activity of serum or plasma samples, purified polyclonal antibodies or isolated monoclonal antibodies. Here, the sample containing opsonic activity antibodies is added to the pathogen together with phagocytes, and rather than resulting in a membrane attack complex, as with bactericidal antibodies, the pathogen will be opsonized with pathogen-specific antibodies and then destroyed by phagocytes, including neutrophils, eosinophils, or macrophages. The assay for measuring the opsonic activity of pathogen-specific antibodies can further include all components of the complement cascade or fractions thereof to aide or allow opsonization of the pathogen, or may include no complement, since antibodies, such as IgG, can pathogen-dependent solely act as opsonin molecules. The assay for measuring opsonic activity will need to detect bacterial growth without interference by the phagocytes, therefore the phagocytes may be removed (e.g., filtration or antibody based cell sorting) or otherwise inactivated (e.g., eukaryotic growth inhibitors). Alternatively, a metabolic indicator that is specific to the bacterial metabolism may also be used.

Assay Components

Sample.

Typically the sample tested in the assay will be a sample having unknown bactericidal activity. The sample will generally be plasma or serum, or a component thereof, taken from a human or animal subject that has been vaccinated against a bacterial pathogen of interest. The plasma or serum sample, or component thereof, can also be collected from reconvalescent or infected patients, and from unvaccinated subjects to measure the bactericidal activity status of these individuals. Another source for a sample can be bacterial pathogen-specific isolated polyclonal or purified monoclonal antibodies, which may be used for prophylactic, therapeutic or diagnostic purposes, to be tested for bactericidal activity. Samples used in the assay may be diluted twofold in separate reaction wells to generate a serial dilution of the sample, such as 1:2, 1:4, 1:8, 1:16, 1:32, 1:64, 1:128, 1:256, and 1:512 etc. Other dilutions are also possible, such as threefold or twofold followed by threefold etc. The reaction wells may be in microtiter plates with 96 wells per plate, preferably with more than 96 wells per plate, such as 384 or 1536 reaction wells per plate. Each diluted sample may be combined with a specified number or sample size of bacteria per well and with active complement to form a reaction solution resulting in lysis of bacteria after a specified incubation period, that would be determined empirically by one skilled in the art using routine techniques, and which is generally for a period of 30 to 90 minutes, by a membrane attack complex comprising complement and specific bactericidal antibodies or by the action of complement and phagocytic cells such as neutrophils or macrophages. Additional control samples are usually included from subjects that have not been vaccinated, as well as a sample reaction with heat-inactivated complement to control for potential background bactericidal activity of the assay.

Metabolic Indicator.

Any bactericidal activity in a sample will result in specific killing of the bacteria added to the assay well, usually within 60 min. Any remaining surviving bacteria can then identified by their metabolic activity using a metabolic indicator that can be detected for example by chromogenic or fluorescent detection, such as ALAMARBLUE™ (resazurin), during an additional incubation step allowing the surviving bacteria to grow to sufficient detectable levels. Additional growth medium is supplied in combination with ALAMARBLUE™, and the medium can be Mueller Hinton (MH) broth or even Dulbecco's PBS buffer supplemented with glucose. ALAMARBLUE™ is a chromogenic reduction-oxygenation (redox) indicator and is in its oxygenized state with a blue color. Once becoming reduced in the living bacterial cell, ALAMARBLUE™ turns pink and the absorbance can be measured in a spectrophotometer at a wavelength of 570 nm. A shift of the optimal absorption wavelength may be possible due to a chromatographic influence by the employed reaction solution. In addition, ALAMARBLUE™ in the reduced state emits a fluorescence signal of 590 nm after excitation at a wavelength of 530-560 nm, so it is also a fluorescent indicator. The colorimetric or fluorescent signal produced by the reduced indicator in surviving bacteria is then captured to measure the bactericidal activity of the sample instead of counting surviving bacterial colonies. Other examples of metabolic indicators beside ALAMARBLUE™ are colorimetric redox indicators such as XTT [2,3-bis(2-methoxy-4-nitro-5-sulfophenyl)-2H-tetrazolium-5-carboxanilide], MTT [3(4,5-dimethylthiazol-2-yl)-2,5-diphenyltetrazoliumbromide], INT [2-(4-iodophenyl)-3-(4-nitrophenyl)-5-phenyl tetrazolium chloride], and CTC (5-cyano-2,3-ditolyltetrazolium chloride), or the fluorescent indicator ANS (8-anilino-1-naphthalenesulfonic acid). Other ways to assess bacterial growth is the direct measurement of optical density at 600 nm or 660 nm in the growth medium.

Measuring Survival.

In order to accurately measure the fluorescent or chromogenic signal from the metabolic indicator to determine number of surviving bacteria, the signal is preferably measured at recurrent timepoints throughout at least a portion of the incubation step with the metabolic indicator. The timepoints for measurement are selected to optimize the generation of signal data in linear range of the metabolic indicator while the bacterial growth is in its log-phase and that those data below linear range or above in the saturated phase may be excluded. Since the samples used to determine bactericidal activity are generally tested for the first time, the titer of bactericidal antibodies will usually be unknown and in such situation can vary greatly. There is also a possible bacterial pathogen-dependent difference in growth properties, since the generation time varies between different bacteria. Thus, the desired timepoints within the linear signal range of the metabolic indicator and the log-phase of the pathogen can vary depending on bactericidal activity of the sample and growth properties of the pathogen. The signal development for a MenB strain, such as NZ98/254 was found to be in both the linear range of ALAMARBLUE™ and the log-phase for the bacteria between five to seven hours of incubation (FIG. 5) at a starting inoculum of 500 cells per well. Since every experiment can have varying conditions, the measuring times can be every hour, or fractions thereof, for example, every 5 min, 10 min, 1 hr, 2 hr, etc., every hour up to 8 hr, up to 24 hr, 48 hr, or 96 hr and beyond. Accordingly, the optimal time period can be determined empirically by one skilled in the art using standard techniques. To allow for optimal reaction conditions, the plates are preferably sealed, which may be with an optical seal, to cover the reaction well and to allow for recurrent colorimetric and fluorescent measurements during the incubation time. Not only is the risk of cross-sample contamination dramatically reduced, but evaporation and thus the impact on growth conditions including affecting the indicator metabolism is also avoided. This can be significant with longer incubation times and allows for more flexibility and increased inter-assay and inter-operator accuracy with this assay, which are desirable factors for a high-throughput BCA assay.

Assessing Bactericidal Activity.

By collection of the measured signals from the metabolic indicator over a timecourse involving recurrent measurements, the linear range for the particular assay and pathogen can be determined. The next step includes determination of the highest signal to noise ratio within the linear measurement range. For instance, when the fluorescence signal generated by bacterial growth reaches 80% value of the signal plateau, that particular time point would still be within the linear measurement range while giving a significantly high signal to noise ratio. By setting a predetermined percent signal of maximum value within the linear range for all assays, the inter-assay variability, including strain variations, can be corrected. That percentage can be anywhere within between 1% and 99% of the signal plateau, preferably at 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, more preferably between 50% and 80%, and most preferably as high as possible, but still within linear range, of the signal. If serum samples are used, an additional normalization step can be included to correct for a loss of the fluorescence signal from the ALAMARBLUE™ indicator at high serum concentrations. The raw values of a test sample with active complement can be divided by a corresponding heat inactivated complement dilution series. The resulting normalized values can then be used for the titer calculation, after implementation of curve fitting using a four parameter logistic model (e.g. 4PL). The final bactericidal titers can be defined as the reciprocal sample dilution of the IC50 (inhibitory concentration) resulting in 50% of the surviving bacteria population. This bacteria population is calculated, after the incubation step of predetermined length to reach the linear signal range of the metabolic indicator, as the relative proportion of the number of surviving bacteria that are present before initiation of the bactericidal reaction (t=0 min) and after the bactericidal reaction (generally t=30 to 90 min). Alternatively, a control culture without bactericidal antibodies is incubated for the same length as the bactericidal reaction (generally t=30 to 90 min) and then exposed to the same incubation step of predetermined length to measure the growth of surviving bacteria in the linear range.

Kits

The methods and compositions disclosed herein may be embodied in a kit for the practice of the assays. In one aspect, the kits for use in methods and compositions as disclosed herein can include (a) a quantity of the pathogen of interest, (b) a quantity of active or inactive complement, (c) a liquid medium to sustain growth of the pathogen, (d) a metabolic indicator, (e) an antibody standard with known bactericidal activity, (f) an antibody sample with known or unknown bactericidal activity.

High-Throughput Device

The methods and compositions disclosed herein may be embodied in a high-throughput device for the implementation of the assays. In one aspect, the device for use in methods and compositions as disclosed herein can include: (a) an assay vessel, (b) a pathogen source sealed for biosafety and containment and fluidly coupled to the assay vessel, (c) a source of active or inactive complement fluidly coupled to the assay vessel, (d) a source of liquid medium to sustain growth of the pathogen fluidly coupled to the assay vessel, (e) a metabolic indicator source fluidly coupled to the assay vessel, (f) a source of an antibody standard with known bactericidal activity fluidly coupled to the assay vessel, (g) a source of an antibody sample with known or unknown bactericidal activity, sealed for biosafety and containment and fluidly coupled to the assay vessel, (h) a colorimetric and/or a fluorescence signal generator and detector. The listed components (a) to (h) are not necessarily in logical order and can be further combined to result in a reduced number of components, or additional components can be added as required for execution of the automated high-throughput assay using the device.

General

The term "comprising" encompasses "including" as well as "consisting" e.g., a composition "comprising" X may consist exclusively of X or may include something additional e.g., X+Y.

The word "substantially" does not exclude "completely" e.g., a composition which is "substantially free" from Y may be completely free from Y. Where necessary, the word "substantially" may be omitted from the definition of the invention. The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g., as in Ph Eur general chapter 5.2.3.

Identity between polypeptide sequences is preferably determined by the Smith-Waterman homology search algorithm as implemented in the MPSRCH program (Oxford Molecular), using an affine gap search with parameters gap open penalty=12 and gap extension penalty=1.

EXAMPLE

Example 1

Comparison of Bactericidal Titers Against Different *N. meningitidis* Strains by Using Conventional and Fluorescence Readouts Overview.

This example demonstrates the correlation between the standard and the fluorescent bactericidal assay (BCA).

Standard Bactericidal Assay.

The standard bactericidal assay was performed as follows: test sera from human subjects vaccinated with MenB recombinant protein+/−OMV and from non-vaccinated individuals were manually diluted twofold from 1:2 to 1:512 in a 96 well microtiter plate. The total reaction volume for the assay was 80 ul consisting of 40 ul of diluted test serum, 20 ul of active complement and 20 ul of diluted bacteria ($1.3 \times 10^4$ cells/ml). The reaction was incubated in 5% CO2 at 37 C for 1 h (t=60 at completion). The t=60 reactions, as well as t=0 controls, were streaked out by spot and tilt method in duplicates onto agar plates and incubated for 18 h at 37 C. Colonies were then counted to determine the cfu and the titer was calculated as the reciprocal dilution at 50% killing.

Automated Fluorescent Bactericidal Assay.

Automated serial dilution of human test sera from vaccinated and non-vaccinated individuals was performed over a range from 1:2 to 1:512 in a 384 well microtiter plate, followed by automated dispension of bacteria and complement to final assay volume of 20 ul consisting of 10 ul of diluted test serum, 5 ul active complement, and 5 ul of bacteria ($1 \times 10^5$ cells/ml). After a 1 h incubation at 37 C in 5% CO2, 20 ul of development mix without agarose (20 ul MH broth+15% AlamarBlue) was automatically dispensed into each well. The plate was then closed with an optically clear plastic seal and incubated overnight, whereas the fluorescence signal was measured automatically every hour to assure that the bacterial growth rate reached 90% value of the signal plateau within the linear measurement range for a highest signal to noise ratio. After normalization of the signal with human serum without detectable bactericidal activity and curve fitting, the titer was calculated as the reciprocal dilution of IC50, defined as 50% of the surviving population at t=60 min incubation of the bacteria with sera and complement.

Results and Conclusions.

Figure 4:
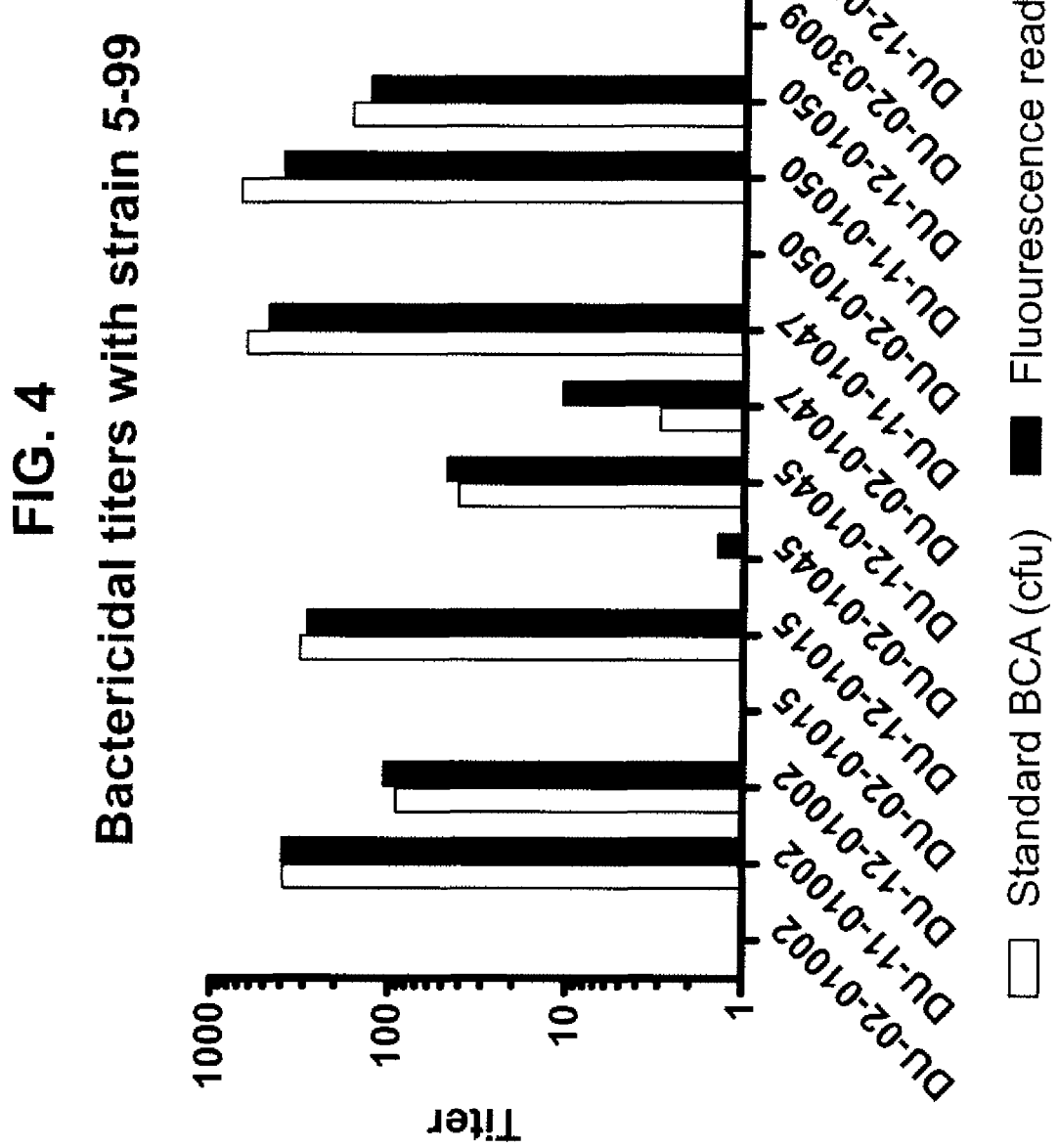
FIG. 4 depicts the calculated titers from the assay shown in FIG. 3. Human sera tested in the bactericidal assay were DU-02 preimmune sera, and DU-11 and DU-12 sera which were post 3rd dose. The geomean titer of all post immunization sera was 191 using the agar based readout and 173 using the fluorescence based readout method. Five of six preimmune sera had titers of <4 in both assays. Fluorescence development time was 7 hr.

The high-throughput (HT)-BCA has been shown to perform equally well in titer determination as the traditional BCA in studies where the same clinical test samples are parallel assayed using the same dilution factors of sample sera for both assays. FIGS. 1-4 demonstrate the good correlation between standard and fluorescent bactericidal assays against different strains of serogroup B *N. meningitidis* (NZ98-254, 44/76-SL, and 5-99; see also FIG. 6 for MenB strain NZ98-254). In addition, FIG. 4 depicts the calculated geometric mean titers for post-vaccination sera which were 191 for the agar based readout and 173 using the fluorescence based readout method. Also, five out of six pre-immune sera had titers of <4 in both assays.

Example 2

Assay Optimization

Signal Development.

Figure 5:
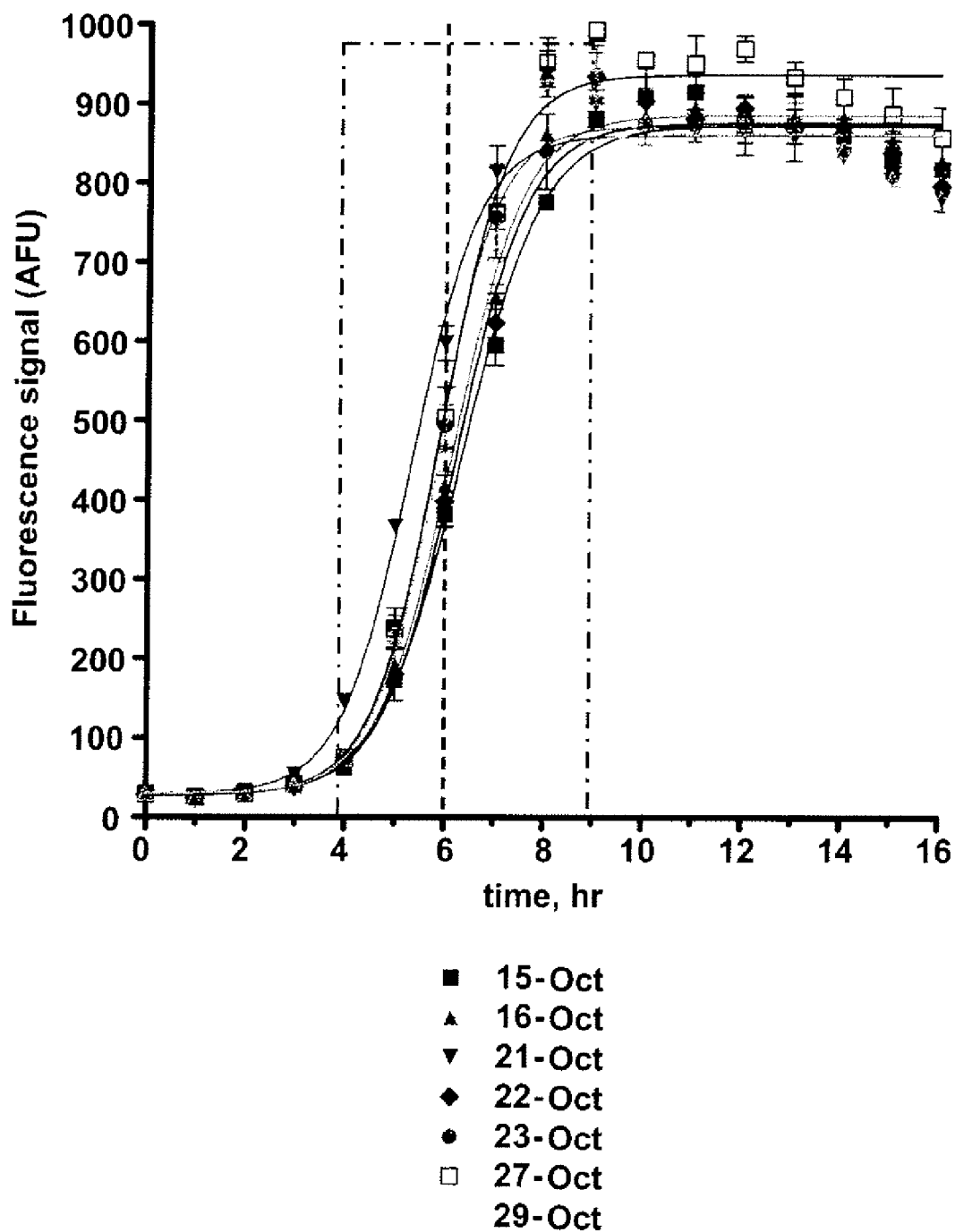
FIG. 5 shows a bacterial growth curve and the resulting fluorescence signals generated by the growth of NZ98/254 in microtiter plates in 7 independent experiments. Titer calculations were performed using data from each hourly time point at 4 to 9 hr post bactericidal reaction (grey boxed area).

In the first step, a bacterial growth curve was generated by plotting fluorescence signal changes over a time range from no detectable *Neisseria meningitidis* serogroup B strain NZ98/254 bacterial growth until the time point when bacterial growth saturation has been reached. The fluorescent BCA was performed as described above, using test sera from human subjects vaccinated with MenB recombinant protein+/−OMV and from non-vaccinated individuals. A total of seven independent experiments were performed and data from hourly time points starting at 4 h until 9 h were used for further analysis (FIG. 5).

Time Point Determination.

Figure 6I:
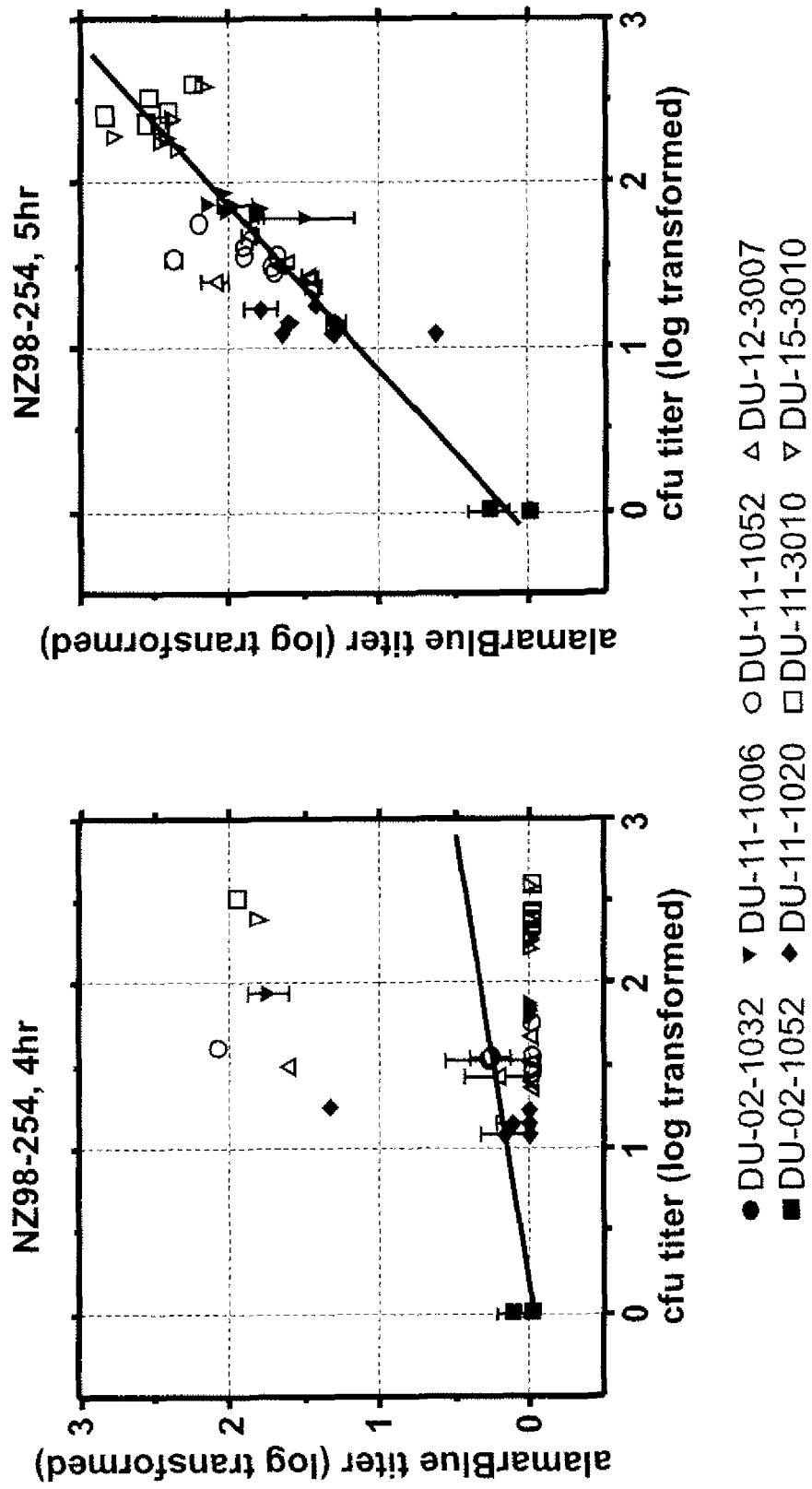
FIG. 6 demonstrates the correlation of titers determined by fluorescence signal (y-axis) and conventional assay (x-axis) at multiple time points during the post-bactericidal reaction against the MenB NZ98-254 strain. Titer calculations were performed using data from each hourly time point at 4 to 9 hr post bactericidal reaction.

FIG. 6 illustrates that the bactericidal antibody titer determination should be taken when the fluorescence signal is a linear measurement of bacterial numeration. Based on the growth curve (FIG. 5), one would expect the time to be 5 to 7 hr post-bactericidal reaction. Alternatively, one can choose a time point for each individual experiment. For instance, when the fluorescence signal generated by bacterial growth reaches 90% value of the signal plateau, that particular time point would still be within the linear measurement range while giving a highest signal to noise ratio. The correlation analysis against the titer calculated at time points when the arbitrary fluorescence units (AFU) are ~90% of max has also been included (Table 1).

TABLE 1

Correlation analysis against titer calculated at time points post bactericidal reaction when AFU is ~90% of maximum signal plateau.
$y = a + b*x$

| Time | A | b | R2 |
|---|---|---|---|
| 4 | 0.039 | 0.133 | 0.045 |
| 5 | 0.117 | 1.024 | 0.932 |
| 6 | 0.160 | 0.992 | 0.950 |
| 7 | 0.198 | 0.909 | 0.934 |
| 8 | 0.240 | 0.813 | 0.927 |
| 9 | 0.103 | 0.793 | 0.945 |
| AFU | 0.187 | 0.907 | 0.935 |

Serum Effect.

Figure 7I:
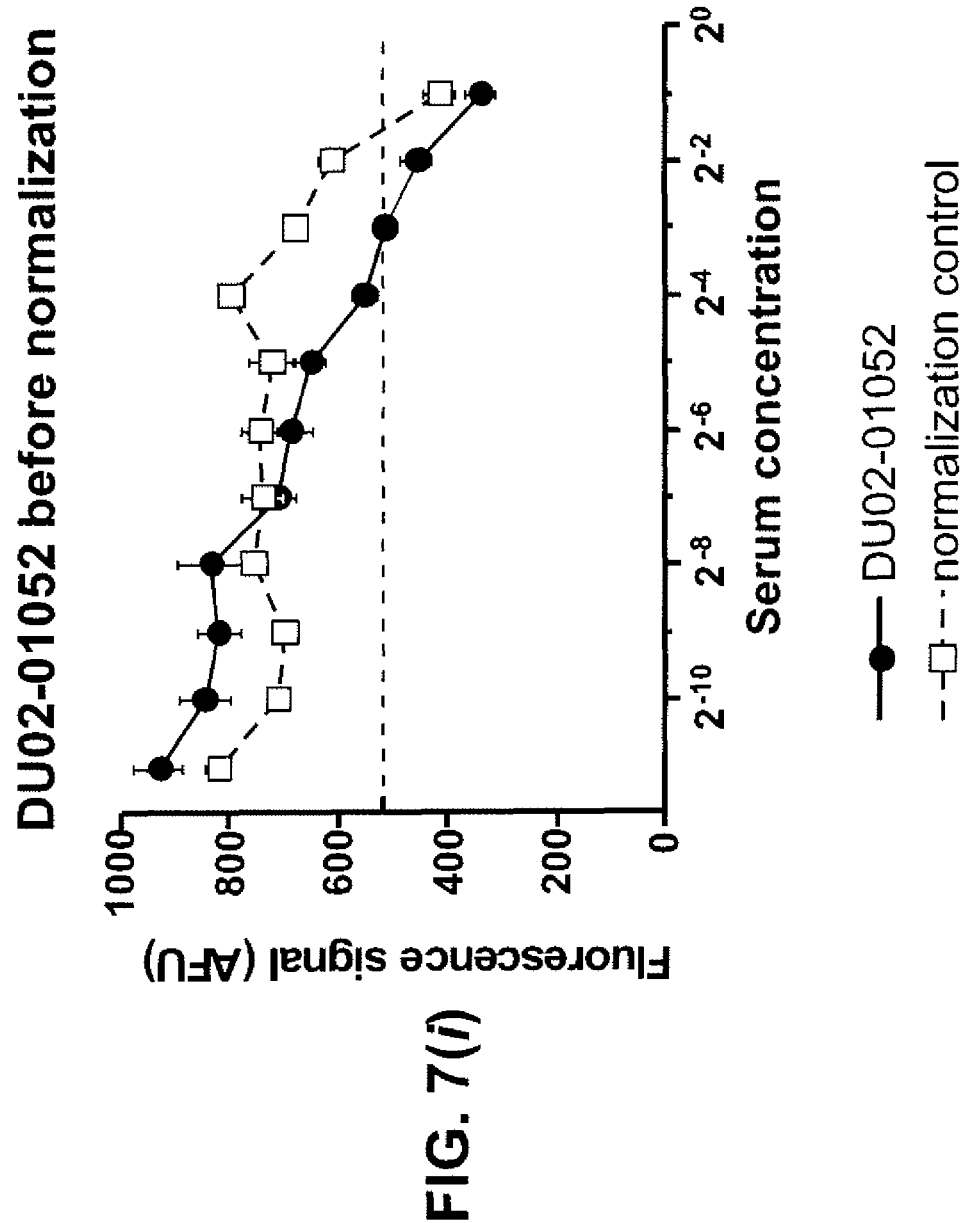
FIG. 7 demonstrates the correction of a serum effect on the resulting titer. The fluorescence signal was quenched by high serum concentration, so normalization was needed. Raw values of test sample DU02-01052 with active complement (A; dark circles) were divided by corresponding heat inactivated complement dilution series (A; grey squares). The normalized values (B) were used for titer calculation. Black bars indicate IC50 cutoff.
Figure 7:
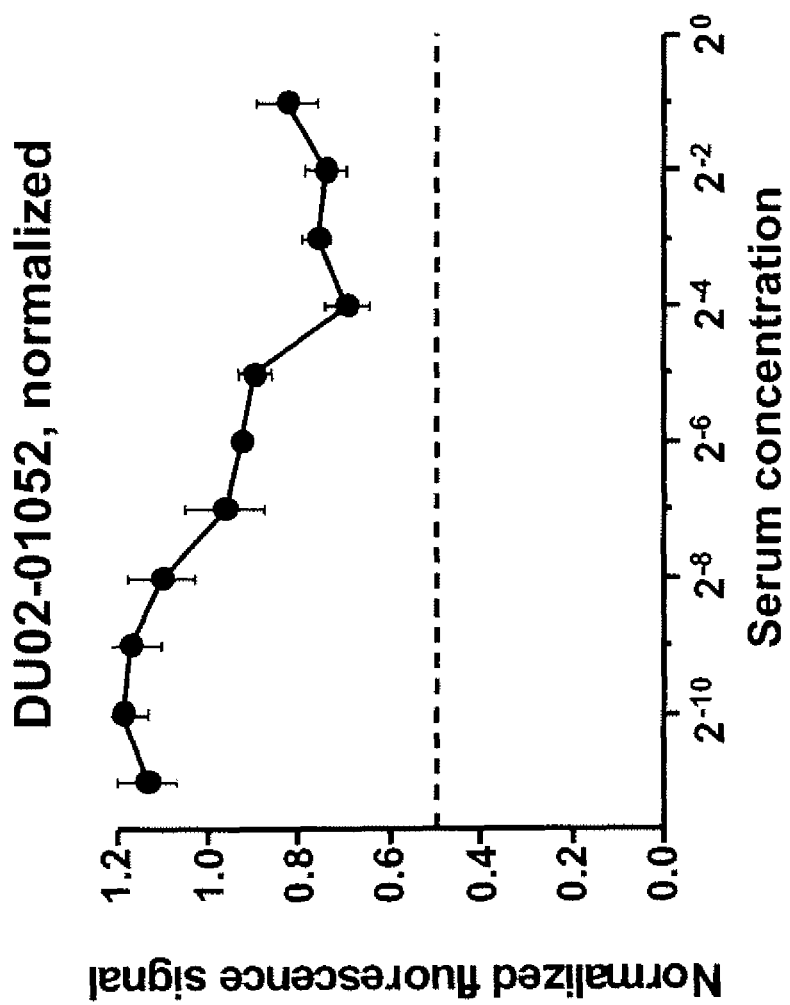

Since the fluorescence signal is subjected to quenching or otherwise lowered by high serum concentration, the raw values of test sample DU02-01052 with active complement were divided by corresponding heat inactivated complement dilution series. The resulting normalized values were then used for the titer calculation. After normalization of the data to remove the serum effect, the titers resulting from the fluorescent readout method showed good correlation with the titers resulting from the standard readout method (FIG. 7).

Example 3

Data Analysis

Normalization Process.

For each day's experiment, the serum normalization controls are run, in triplicate at each dilution point. As indicated above, high serum concentrations were observed to inhibit the fluorescent signal of ALAMARBLUE™. Therefore, a serum that was heated to inactivate the complement was used to normalize the signal to correct for such quenching or other signal loss. If the serum which was being used as the complement source for the experiment was from the same species as the experimental sera, then that serum could also be used for normalization. It was then present in the reaction mixtures for two different purposes. In one case, the serum was present as the complement source at a constant concentration (in which case the serum was not heat inactivated). In the other case, the serum was present in a separate set of reactions as the normalization control in which the serum was heated to inactivate the complement and in serial dilution form matching the serial dilutions of the experimental sera for which is was serving as a normalization control. However, if the complement-source serum was from a different species than the experimental sera, then a separate serum of the same species as the experimental sera would have been used to fulfill the role of the heat-inactivated serial dilution serum normalization control.

The controls with the heat inactivated complement were diluted at the same dilution factors as the experimental sample and were measured at the same time points. A normalization factor was computed for each time-point for each dilution by taking the median of the triplicate AFUs. The AFU value for each test serum was divided by the normalization factor for the corresponding time-point and dilution of the normalization control. This put the normalized values for test sera with no killing activity near 1.0. If a test sample had to be pre-diluted due to very high titer, such that there was no serum normalization control at a corresponding dilution, then the factor for the highest dilution which was available was used instead.

Curve Fitting Process.

A four parameter logistic curve, described by the equation below, was fitted to the concentration of the test serum (relative to neat serum) and response data. The curve bottom was constrained to be between 0 and 0.15, the curve top was constrained to be between 0.8 and 1.5, and the Hill slope was constrained to be between −3.0 and +3.0.

$$\text{response} = \text{bottom} + \frac{\text{top} - \text{bottom}}{1 + \left(\frac{\text{Concentration}}{IC_{50}}\right)^{-Hill}}$$

Growth Curves.

The observed signal in the assays was the composition of several response functions. The bactericidal activity of antibody with respect to antibody concentration, the growth of bacteria over time as they saturate the growth media, and the metabolism of ALAMARBLUE™ as it becomes depleted from the media were all sigmoid functions. It was important to inspect the "growth" curves, as determined by controls over the time-course, to ensure that the time point chosen for IC50 determination occurred near the steepest part of the growth curve.

For the time point determination, it is important to use the time point when the control bacteria are still growing rapidly and the signal from the metabolic indicator is still changing. If the signal is no longer changing, there are a number of possible reasons. The culture may no longer be growing; the signal from the metabolic indicator could be saturated; or the culture may have run out of the metabolic indicator to metabolize, even though the bacteria themselves are still growing.

In one system using human sera, the fluorescent signal changed rapidly until it suddenly reached saturation (or exhaustion of ALAMARBLUE™ supply to metabolize). Due to this shape of the growth curve, a good time point for IC50 determination was the last reading before the signal crossed 90% of its maximal value. In other systems, the combination of bacterial strain and non-human complement source exhibited a growth curve in which the signal slows gradually rather than suddenly as it approaches saturation. For such systems, the 90% criteria was not suitable since the last time point before 90% of the maximum was already starting to show substantial saturation, and was therefore not suitable. In such case, a different heuristic was applied. The interval between two consecutive readings during which the signal has increased the most was identified and the later of the two consecutive readings was used as the time point for IC50 determination.

What we claim is:

1. A high-throughput method of determining bactericidal activity of a test sample comprising: (a) providing a sealed, non-gel fluid comprising an amount of a pathogen, the test sample, a metabolic indicator, and a potentiator, wherein the fluid has been incubated for a time period sufficient for the test sample to kill a portion of the pathogen if the test sample comprises bactericidal or opsonic activity; (b) measuring the metabolic indicator in the sealed, non-gel fluid comprising the test sample at three or more time points during a second incubation; and (c) determining the bactericidal activity of the test sample using a control using the measurements at the three or more time points.

2. The method of claim 1 wherein the metabolic indicator is a chromogenic compound or a fluorescent compound.

3. The method of claim 2 wherein said metabolic indicator is resazurin.

4. The method of claim 2, wherein the pathogen is selected from the group consisting of *N. meningitidis*, *N. gonorrhoeae*, *Streptococcus pyogenes*, *Streptococcus agalactiae*, *Streptococcus pneumoniae*, *H. influenzae*, *Staphylococcus aureus*, *Haemophilus influenza* B, *H. pylori*, meningitis/sepsis associated *E. coli*, Nontypeable *Haemophilus influenzae*, and uropathogenic *E. coli*.

5. The method of claim 1, wherein the potentiator is complement when assaying bactericidal activity or phagocytic cells and optionally complement when assaying opsonic activity.

6. The method of claim 5 wherein the phagocytic cells are neutrophils or macrophages.

7. The method of claim 5, wherein the phagocytic cells are inactivated prior to the second incubation.

8. The method of claim 5, wherein the metabolic indicator does not respond to the phagocytic cells' metabolic activity.

9. The method of claim 5 wherein the complement is active complement.

10. The method of claim 9, wherein said active complement is obtained from the group consisting of human, rabbit, baby-rabbit, other animal origin, or recombinant.

11. The method of claim 5, wherein the complement is inactive.

12. The method of claim 1, wherein said non-gel fluid contains no agarose or any other gelling agent used to form a solid growth surface for bacteria.

13. The method of claim 1, wherein said sealed, non-gel fluid is sealed prior to incubation of the pathogen and the test sample and measurements to prevent evaporation of said fluid.

14. The method of claim 1, wherein said sealed, non-gel fluid is sealed after incubation of the pathogen and the test sample and measurements to prevent evaporation of said fluid.

15. The method of claim 13, wherein said sealing comprises an optically clear seal to perform colorimetric and/or fluorimetric measurements without removal of said seal.

16. The method of claim 1, wherein said test sample is an isolated antibody, serum or plasma of human or animal origin.

17. The method of claim 16, wherein said serum or plasma test sample is obtained from a subject that was inoculated with a vaccine, a vaccine candidate or a vaccine component directed against the pathogen.

18. The method of claim 17, wherein the vaccine, the vaccine candidate or the vaccine component comprises one or more of a GNA1870 antigen, a GNA2132 antigen, and a NadA antigen.

19. The method of claim 1, wherein said test sample is an isolated antibody.

20. The method of claim 1, wherein said test sample is a recombinant antibody.

21. The method of claim 1, further comprising at least a second non-gel fluid wherein the second non-gel fluid comprises a dilution of the test sample in the first non-gel fluid.

22. The method of claim 21, wherein the dilution can be twofold, threefold, or fourfold or a repetitive dilution step of twofold dilution followed by twofold dilution, twofold dilution followed by threefold dilution, threefold dilution followed by threefold dilution, or fourfold dilution followed by fourfold dilution.

23. The method of claim 21, wherein the non-gel fluids are incubated and measured in microtiter plates selected from the group consisting of 96, 384, and 1536 reaction wells per plate.

24. The method of claim 23, wherein said microtiter plates have at least 384 reaction wells per plate.

25. The method of claim 23, wherein said microtiter plates have at least 96 reaction wells per plate.

26. The method of claim 1, wherein said measuring comprises repeated readings of said test sample at predetermined time points for determination of the bactericidal activity.

27. The method of claim 26, wherein said predetermined time points are selected from the group consisting of every minute, every hour and fractions thereof.

28. The method of claim 1, wherein at least three of said measured time points are in the linear measurement range of the metabolic indicator to measure the pathogen's growth.

29. The method of claim 28, wherein said measurements are fluorescence signals representing bacterial growth.

30. The method of claim 29, wherein the highest signal to noise ratio of about 50% to about 80% of the fluorescence signal plateau is within linear measurement range of the metabolic indicator to measure the pathogen's growth.

31. The method of claim 29, wherein said signal to noise ratio can be anywhere in between 1% to 99% of the fluorescence signal plateau.

32. The method of claim 1, wherein steps a) to c) are fully automated.

33. The method of claim 1, wherein said determining step comprises correcting signal loss at high serum concentration by normalization with a control containing inactivated complement at a concentration approximately equal to the test sample.

34. The method of claim 21, wherein said determining step comprises correcting signal loss at high serum concentration by normalization with at least two controls containing inactivated complement wherein the second control comprises a dilution of the first control that is equal to the dilution of the second non-gel fluid from the first nongel fluid.

35. The method of claim 1, wherein the control is a sample consisting of the pathogen, the metabolic indicator, and the potentiator.

36. The method of claim 1, wherein the control is a sample which does not comprise bactericidal antibodies.

37. The method of claim 1, wherein the control comprises a serial dilution series of the test sample.

38. The method of claim 5, wherein the control is a sample comprising phagocytic cells.

\* \* \* \* \*